(12) United States Patent
Nettekoven et al.

(10) Patent No.: US 7,648,979 B2
(45) Date of Patent: Jan. 19, 2010

(54) 5-AMIDO-(1H-INDOL-2-YL)-PIPERAZIN-1-YL-METHANONE DERIVATIVES

(75) Inventors: Matthias Nettekoven, Grenzach-Wyhlen (DE); Jean-Marc Plancher, Hagenthal-le-Bas (FR); Hans Richter, Grenzach-Wyhlen (DE); Olivier Roche, Folgensbourg (FR); Sven Taylor, Riedisheim (FR)

(73) Assignee: Hoffmann-La Roche Inc., Nutley, NJ (US)

( * ) Notice: Subject to any disclaimer, the term of this patent is extended or adjusted under 35 U.S.C. 154(b) by 33 days.

(21) Appl. No.: 12/020,637

(22) Filed: Jan. 28, 2008

(65) Prior Publication Data

US 2008/0188487 A1 Aug. 7, 2008

(30) Foreign Application Priority Data

Feb. 7, 2007 (EP) .................................. 07101883

(51) Int. Cl.
*A61K 31/404* (2006.01)
*A61P 3/04* (2006.01)
*C07D 401/04* (2006.01)
*C07D 209/42* (2006.01)

(52) U.S. Cl. .................. 514/218; 514/252.11; 540/575; 544/357

(58) Field of Classification Search ........................ None
See application file for complete search history.

(56) References Cited

U.S. PATENT DOCUMENTS

2005/0282864 A1 12/2005 McArthur et al.
2006/0160855 A1 7/2006 Nettekoven et al.

FOREIGN PATENT DOCUMENTS

WO WO 03/064413 8/2003
WO WO 2007/115938 10/2007

OTHER PUBLICATIONS

Masaki et al., Endocrinol, 144, pp. 2741-2748 (2003).
Hancock et al., European J. of Pharmacol., 487, pp. 183-197 (2004).
Timmermann, H., J. Med. Chem., 33, pp. 4-11 (1990).
Scapecchi et al., Bioorg. Med. Chem., 12, pp. 71-85 (2004).
Zaragoza et al., J. Med. Chem., 47, pp. 2833-2838 (2004).
Mederski et al., Tetrahedron, 55, pp. 12757-12770 (1999).
Lindwall et al., J. Org. Chem., 18, pp. 345-357 (1953).
Kumar, K., Org. Letters, 6, pp. 7-10 (2004).

*Primary Examiner*—Emily Bernhardt
(74) *Attorney, Agent, or Firm*—George W. Johnston; Dennis P. Tramaloni; Brian C. Remy

(57) ABSTRACT

The present invention relates to compounds of formula I

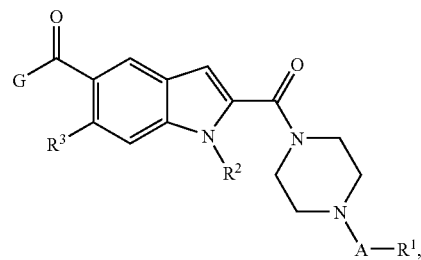

wherein A, G and $R^1$ to $R^3$ are as defined in the description and claims, and pharmaceutically acceptable salts thereof. The compounds are useful for the treatment and/or prevention of diseases which are associated with the modulation of H3 receptors.

22 Claims, No Drawings

5-AMIDO-(1H-INDOL-2-YL)-PIPERAZIN-1-YL-METHANONE DERIVATIVES

PRIORITY TO RELATED APPLICATIONS

This application claims the benefit of European Patent Application No. 07101883.2, filed Feb. 7, 2007, which is hereby incorporated by reference in its entirety.

BACKGROUND OF THE INVENTION

The present invention relates to novel 5-amido-(1H-indol-2-yl)-piperazin-1-yl-methanone derivatives, their manufacture, pharmaceutical compositions containing them and their use as medicaments. The active compounds of the present invention are antagonists and/or inverse agonists at the histamine 3 receptor (H3 receptor).

Histamine (2-(4-imidazolyl) ethylamine) is one of the aminergic neurotransmitters which is widely distributed throughout the body, e. g. the gastrointestinal tract (Burks 1994 in Johnson L. R. ed., Physiology of the Gastrointestinal Tract, Raven Press, N.Y., pp. 211-242). Histamine regulates a variety of digestive pathophysiological events like gastric acid secretion, intestinal motility (Leurs et al., Br J. Pharmacol. 1991, 102, pp 179-185), vasomotor responses, intestinal inflammatory responses and allergic reactions (Raithel et al., Int. Arch. Allergy Immunol. 1995, 108, 127-133). In the mammalian brain, histamine is synthesized in histaminergic cell bodies which are found centrally in the tubero-mammillary nucleus of the posterior basal hypothalamus. From there, the histaminergic cell bodies project to various brain regions (Panula et al., Proc. Natl. Acad. Sci. USA 1984, 81, 2572-2576; Inagaki et al., J. Comp. Neurol 1988, 273, 283-300).

According to current knowledge, histamine mediates all its actions in both the CNS and the periphery through four distinct histamine receptors, the histamine H1, H2 H3 and H4 receptors.

H3 receptors are predominantly localized in the central nervous system (CNS). As an autoreceptor H3 receptors constitutively inhibit the synthesis and secretion of histamine from histaminergic neurons (Arrang et al., Nature 1983, 302, 832-837; Arrang et al., Neuroscience 1987, 23, 149-157). As heteroreceptors, H3 receptors also modulate the release of other neurotransmitters such as acetylcholine, dopamine, serotonin and norepinephrine among others in both the central nervous system and in peripheral organs, such as lungs, cardiovascular system and gastrointestinal tract (Clapham & Kilpatrik, Br. J. Pharmacol. 1982, 107, 919-923; Blandina et al. in The Histamine H3 Receptor (Leurs R L and Timmermann H eds, 1998, pp 27-40, Elsevier, Amsterdam, The Netherlands). H3 receptors are constitutively active, meaning that even without exogenous histamine, the receptor is tonically activated. In the case of an inhibitory receptor such as the H3 receptor, this inherent activity causes tonic inhibition of neurotransmitter release. Therefore it may be important that a H3R antagonist would also have inverse agonist activity to both block exogenous histamine effects and to shift the receptor from its constitutively active (inhibitory) form to a neutral state.

The wide distribution of H3 receptors in the mammalian CNS indicates the physiological role of this receptor. Therefore the therapeutic potential as a novel drug development target in various indications has been proposed.

The administration of H3R ligands—as antagonists, inverse agonists, agonists or partial agonists—may influence the histamine levels or the secretion of neurotransmitters in the brain and the periphery and thus may be useful in the treatment of several disorders. Such disorders include obesity, (Masaki et al; Endocrinol. 2003, 144, 2741-2748; Hancock et al., European J. of Pharmacol. 2004, 487, 183-197), cardiovascular disorders such as acute myocardial infarction, dementia and cognitive disorders such as attention deficit hyperactivity disorder (ADHD) and Alzheimer's disease, neurological disorders such as schizophrenia, depression, epilepsy, Parkinson's disease, and seizures or convulsions, sleep disorders, narcolepsy, pain, gastrointestinal disorders, vestibular dysfunction such as Morbus Meniere, drug abuse and motion sickness (Timmermann, J. Med. Chem. 1990, 33, 4-11).

It is therefore an object of the present invention to provide selective, directly acting H3 receptor antagonists respectively inverse agonists. Such antagonists/inverse agonists are useful as therapeutically active substances, particularly in the treatment and/or prevention of diseases which are associated with the modulation of H3 receptors.

SUMMARY OF THE INVENTION

The invention is concerned with the compounds of formula I:

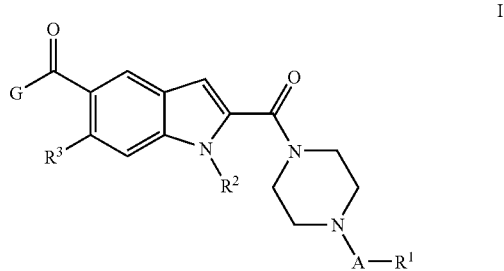

and pharmaceutically acceptable salts thereof, wherein A, G and $R^1$-$R^3$ are as defined in the detailed description and claims. In addition, the present invention relates to the methods of manufacturing and using the compounds of formula I as well as pharmaceutical compositions containing them. The compounds of formula I are antagonists and/or inverse agonists at the histamine 3 receptor (H3 receptor) and may be useful in treating obesity and other disorders associated with the H3 receptor.

DETAILED DESCRIPTION OF THE INVENTION

In the present description the term "alkyl", alone or in combination with other groups, refers to a branched or straight-chain monovalent saturated aliphatic hydrocarbon radical of one to twenty carbon atoms. In certain preferred embodiments, the alkyl group has one to sixteen carbon atoms, more preferably one to ten carbon atoms.

The term "lower alkyl" or "$C_1$-$C_7$-alkyl", alone or in combination, signifies a straight-chain or branched-chain alkyl group with 1 to 7 carbon atoms. In certain preferred embodiments, the lower alkyl or $C_1$-$C_7$-alkyl group is a straight or branched-chain alkyl group with 1 to 6 carbon atoms and particularly preferred are straight or branched-chain alkyl groups with 1 to 4 carbon atoms. Examples of straight-chain and branched $C_1$-$C_7$ alkyl groups are methyl, ethyl, propyl, isopropyl, butyl, isobutyl, tert.-butyl, the isomeric pentyls, the isomeric hexyls and the isomeric heptyls, preferably methyl and ethyl and most preferred methyl.

The term "cycloalkyl" or "$C_3$-$C_7$-cycloalkyl" denotes a saturated carbocyclic group containing from 3 to 7 carbon atoms. Examples include cyclopropyl, cyclobutyl, cyclopentyl, cyclohexyl and cycloheptyl. Especially preferred are cyclobutyl and cyclopentyl.

The term "lower cycloalkylalkyl" or "$C_3$-$C_7$-cycloalkyl-$C_1$-$C_7$-alkyl" refers to lower alkyl groups as defined above wherein at least one of the hydrogen atoms of the lower alkyl group is replaced by cycloalkyl. A preferred example is cyclopropylmethyl.

The term "alkoxy" or "lower alkoxy" refers to the group R'—O—, wherein R' is lower alkyl and the term "lower alkyl" has the previously given significance. Examples of lower alkoxy groups are methoxy, ethoxy, n-propoxy, isopropoxy, n-butoxy, isobutoxy, sec.-butoxy and tert.-butoxy, preferably methoxy and ethoxy and most preferably ethoxy.

The term "lower hydroxyalkyl" or "hydroxy-$C_1$-$C_7$-alkyl" refers to lower alkyl groups as defined above wherein at least one of the hydrogen atoms of the lower alkyl group is replaced by a hydroxy group. Examples of lower hydroxyalkyl groups are hydroxymethyl and hydroxyethyl.

The term "lower alkoxyalkyl" or "$C_1$-$C_7$-alkoxy-$C_1$-$C_7$-alkyl" refers to lower alkyl groups as defined above wherein at least one of the hydrogen atoms of the lower alkyl group is replaced by an alkoxy group. Examples of lower hydroxyalkyl groups are methoxy and ethoxy. Among the preferred lower alkoxyalkyl groups are 2-methoxyethyl and 3-methoxypropyl.

The term "halogen" refers to fluorine, chlorine, bromine or iodine. In certain preferred embodiments the halogen is fluorine, chlorine or bromine.

The term "lower halogenalkyl" or "halogen-$C_1$-$C_7$-alkyl" refers to lower alkyl groups as defined above wherein at least one of the hydrogen atoms of the lower alkyl group is replaced by a halogen atom. In certain preferred embodiments at least one of the hydrogen atoms of the lower alkyl group is replaced by fluoro or chloro, most preferably fluoro. Among the preferred halogenated lower alkyl groups are trifluoromethyl, difluoromethyl, trifluoroethyl, 2,2-difluoroethyl, fluoromethyl and chloromethyl, with trifluoromethyl or 2,2-difluoroethyl being especially preferred.

The term "alkylsulfonyl" or "lower alkylsulfonyl" refers to the group R'—S(O)$_2$—, wherein R' is lower alkyl and the term "lower alkyl" has the previously given significance. Examples of alkylsulfonyl groups are methylsulfonyl and ethylsulfonyl.

The term "phenylsulfonyl" refers to the group R"—S(O)$_2$—, wherein R" is phenyl.

The term "lower alkanoyl" refers to the group —CO—R', wherein R' is lower alkyl and the term "lower alkyl" has the previously given significance. Preferred is a group —CO—R', wherein R' is methyl, meaning an acetyl group.

The term "lower phenylalkyl" or "phenyl-$C_1$-$C_7$-alkyl" refers to lower alkyl groups as defined above wherein at least one of the hydrogen atoms of the lower alkyl group is replaced by a phenyl group. Preferred lower phenylalkyl groups are benzyl or phenethyl.

The term "heteroaryl" in general refers to an aromatic 5- or 6-membered ring which can comprise one, two or three atoms independently selected from nitrogen, oxygen and sulphur (such as but not limited to furyl, pyridyl, 1,2-, 1,3- and 1,4-diazinyl, thienyl, isoxazolyl, oxazolyl, imidazolyl, and pyrrolyl). The term "heteroaryl" further refers to bicyclic aromatic groups comprising two 5- or 6-membered rings, in which one or both rings can contain one, two or three atoms independently selected from nitrogen, oxygen and sulphur (such as but not limited to indole or quinoline). A preferred heteroaryl group is pyridyl.

The term "form a 5- or 6-membered heterocyclic ring optionally containing a further heteroatom of nitrogen, oxygen or sulfur" refers to a N-heterocyclic ring, which may optionally contain a further nitrogen, oxygen or sulfur atom, such as (but not limited to) pyrrolidinyl, imidazolyl, oxazolidinyl, isoxazolidinyl, thiazolidinyl, isothiazolidinyl, piperidinyl, pyrazinyl, morpholinyl or thiomorpholinyl.

The term "pharmaceutically acceptable salts" refers to those salts which retain the biological effectiveness and properties of the free bases or free acids, which are not biologically or otherwise undesirable. The salts are formed with inorganic acids such as hydrochloric acid, hydrobromic acid, sulfuric acid, nitric acid, phosphoric acid and the like, preferably hydrochloric acid, and organic acids such as acetic acid, propionic acid, glycolic acid, pyruvic acid, oxylic acid, maleic acid, malonic acid, salicylic acid, succinic acid, fumaric acid, tartaric acid, citric acid, benzoic acid, cinnamic acid, mandelic acid, methanesulfonic acid, ethanesulfonic acid, p-toluenesulfonic acid, salicylic acid, N-acetylcystein and the like. In addition these salts may be prepared from addition of an inorganic base or an organic base to the free acid. Salts derived from an inorganic base include, but are not limited to, the sodium, potassium, lithium, ammonium, calcium, magnesium salts and the like. Salts derived from organic bases include, but are not limited to salts of primary, secondary, and tertiary amines, substituted amines including naturally occurring substituted amines, cyclic amines and basic ion exchange resins, such as isopropylamine, trimethylamine, diethylamine, triethylamine, tripropylamine, ethanolamine, lysine, arginine, N-ethylpiperidine, piperidine, polymine resins and the like. The compound of formula I can also be present in the form of zwitterions. Particularly preferred pharmaceutically acceptable salts of compounds of formula I are the hydrochloride salts.

The compounds of formula I can also be solvated, e.g. hydrated. The solvation can be effected in the course of the manufacturing process or can take place e.g. as a consequence of hygroscopic properties of an initially anhydrous compound of formula I (hydration). The term "pharmaceutically acceptable salts" also includes physiologically acceptable solvates.

"Isomers" are compounds that have identical molecular formulae but that differ in the nature or the sequence of bonding of their atoms or in the arrangement of their atoms in space. Isomers that differ in the arrangement of their atoms in space and have one or more asymmetric carbon atoms are termed "stereoisomers". Stereoisomers that are not mirror images of one another are termed "diastereoisomers", and stereoisomers that are non-superimposable mirror images are termed "enantiomers", or sometimes optical isomers.

The term "a therapeutically effective amount" of a compound means an amount of compound that is effective to prevent, alleviate or ameliorate symptoms of disease or prolong the survival of the subject being treated. Determination of a therapeutically effective amount is within the skill in the art. The therapeutically effective amount or dosage of a compound according to this invention can vary within wide limits and may be determined in a manner known in the art. Such dosage will be adjusted to the individual requirements in each particular case including the specific compound(s) being administered, the route of administration, the condition being treated, as well as the patient being treated. In general, in the case of oral or parenteral administration to adult humans weighing approximately 70 Kg, a daily dosage of about 0.1 mg to about 5,000 mg, 1 mg to about 1,000 mg, or 1 mg to 100 mg may be appropriate, although the upper limit may be exceeded when indicated. The daily dosage can be administered as a single dose or in divided doses, or for parenteral administration, it may be given as continuous infusion.

The term "pharmaceutically acceptable carrier" is intended to include any and all material compatible with pharmaceutical administration including solvents, dispersion media, coatings, antibacterial and antifungal agents, isotonic and absorption delaying agents, and other materials and compounds compatible with pharmaceutical administration. Except insofar as any conventional media or agent is incompatible with the active compound, use thereof in the compositions of the invention are contemplated. Supplementary active compounds can also be incorporated into the compositions.

Unless otherwise indicated, the term "a compound of the formula" or "a compound of formula" or "compounds of the formula" or "compounds of formula" means any compound selected from the genus of compounds as defined by the formula.

In detail, the present invention relates to the compounds of formula I:

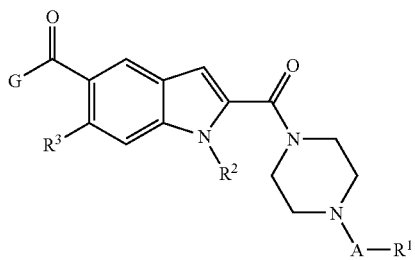

I and pharmaceutically acceptable salts thereof wherein:

A is C(O) or S(O)$_2$;

R$^1$ is selected from the group consisting of:
  (1) lower alkyl,
  (2) lower alkoxy,
  (3) cycloalkyl,
  (4) lower cycloalkylalkyl,
  (5) lower halogenalkyl,
  (6) phenyl unsubstituted or substituted with one to three substituents independently selected from the group consisting of lower alkyl, lower alkoxy, halogen, lower halogenalkyl and cyano, and
  (7) —NR$^4$R$^5$, wherein R$^4$ and R$^5$ independently from each other are selected from the group consisting of lower alkyl, cycloalkyl, lower cycloalkylalkyl, lower halogenalkyl and lower phenylalkyl, or alternatively, R$^4$ and R$^5$ together with the nitrogen atom to which they are attached form a 5- or 6-membered heterocyclic ring optionally containing a further heteroatom of nitrogen, oxygen or sulfur;

R$^2$ is selected from the group consisting of:
  (1) hydrogen,
  (2) lower alkyl,
  (3) cycloalkyl,
  (4) lower cycloalkylalkyl,
  (5) lower hydroxyalkyl,
  (6) lower alkoxyalkyl,
  (7) lower halogenalkyl,
  (8) lower cyanoalkyl,
  (9) lower alkylsulfonyl,
  (10) lower alkanoyl,
  (11) phenylsulfonyl wherein the phenyl ring may be unsubstituted or substituted with one to three substituents independently selected from the group consisting of lower alkyl, halogen, lower alkoxy, lower halogenalkoxy and lower hydroxyalkyl,
  (12) phenyl unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino,
  (13) benzodioxolyl,
  (14) lower phenylalkyl, wherein the phenyl ring may be unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
  (15) heteroaryl unsubstituted or substituted with one or two substituents independently selected from the group consisting of lower alkyl, lower alkoxy, cyano, morpholinyl and halogen;

R$^3$ is hydrogen, halogen or methyl;

G is either G1 or G2:

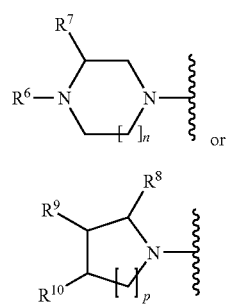

wherein:

R$^6$ is lower alkyl, cycloalkyl, lower cycloalkylalkyl or a heterocyclic ring containing oxygen, and R$^7$ is hydrogen; or alternatively R$^6$ and R$^7$ together are —(CH$_2$)$_m$—, wherein m is 3 or 4, and are bonded to each other to form a ring together with the carbon or nitrogen atom to which they are attached;

n is 1 or 2;

p is 1 or 2;

R$^8$ is hydrogen or lower heterocyclylalkyl;

R$^9$ and R$^{10}$ independently from each other are hydrogen or —NR$^{11}$R$^{12}$; and R$^{11}$ and R$^{12}$ independently from each other are lower alkyl or together with the nitrogen atom to which they are attached form a 5- or 6-membered saturated heterocyclic ring optionally containing a further heteroatom of nitrogen, oxygen or sulfur.

Preferred are compounds of formula I according to the present invention, wherein A is S(O)$_2$, meaning compounds of formula I having the formula

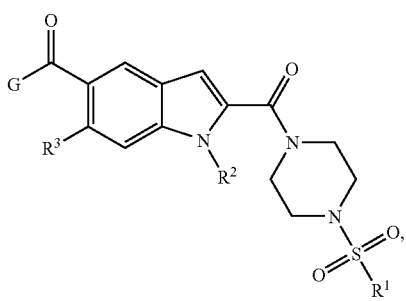

wherein G, $R^1$, $R^2$ and $R^3$ are as defined herein before, and pharmaceutically acceptable salts thereof.

Also preferred are compounds of formula I according to the present invention, wherein A is C(O), meaning compounds of formula I having the formula

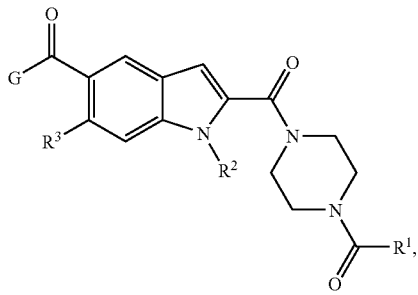

wherein G, $R^1$, $R^2$ and $R^3$ are as defined herein before, and pharmaceutically acceptable salts thereof.

Preferred are furthermore compounds of formula I according to the present invention, wherein $R^1$ is selected from the group consisting of
lower alkyl, lower alkoxy,
cycloalkyl,
phenyl unsubstituted or substituted with one to three groups independently selected from lower alkyl, lower alkoxy, halogen, lower halogenalkyl and cyano, and —$NR^4R^5$, wherein $R^4$ and $R^5$ independently from each other are selected from lower alkyl, cycloalkyl, lower cycloalkylalkyl, lower halogenalkyl and lower phenylalkyl, or wherein $R^4$ and $R^5$ together with the nitrogen atom to which they are attached form a 5- or 6-membered heterocyclic ring optionally containing a further heteroatom of nitrogen, oxygen or sulfur.

More preferred are compounds of formula I according to the invention, wherein $R^1$ is selected from the group consisting of lower alkyl, cycloalkyl and phenyl, with $R^1$ being lower alkyl or cycloalkyl being especially preferred and with $R^1$ being isopropyl or cyclopropyl being most preferred.

Also more preferred are compounds of formula I according to the invention, wherein $R^1$ is —$NR^4R^5$, wherein $R^4$ and $R^5$ independently from each other are lower alkyl or wherein $R^4$ and $R^5$ together with the nitrogen atom they are attached to form a piperidine ring.

Furthermore, compounds of formula I according to the invention are preferred, wherein $R^1$ is lower alkoxy. More preferred are those, wherein A is C(O) and $R^1$ is lower alkoxy, most preferably ethoxy.

Another group of preferred compounds of formula I according to the present invention are those, wherein $R^2$ is selected from the group consisting of hydrogen,
lower alkyl, cycloalkyl, lower cycloalkylalkyl,
lower halogenalkyl,
phenyl unsubstituted or substituted with one to three groups independently selected from lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
pyridyl unsubstituted or substituted with one or two groups independently selected from lower alkyl, lower alkoxy, cyano, morpholinyl and halogen.

Compounds of formula I according to the invention are more preferred, wherein $R^2$ is hydrogen. Also more preferred are compounds of formula I according to the invention, wherein $R^2$ is lower alkyl.

In addition, compounds of formula I according to the invention are preferred, wherein $R^2$ is phenyl unsubstituted or substituted with one to three groups independently selected from lower alkyl, halogen and lower halogenalkyl.

Further preferred are compounds of formula I according to the invention, wherein $R^2$ is pyridyl which is unsubstituted or substituted with one or two groups independently selected from lower alkyl and halogen.

$R^3$ is preferably hydrogen. In case $R^3$ is halogen, chloro or bromo are especially preferred.

A group of preferred compounds of formula I according to the invention are those, wherein G is

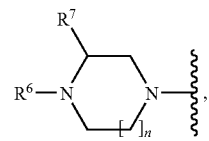

wherein $R^6$ is selected from the group consisting of lower alkyl, cycloalkyl, lower cycloalkylalkyl and a heterocyclic ring containing oxygen, $R^7$ is hydrogen, and n is 1 or 2, and pharmaceutically acceptable salts thereof, meaning these are compounds of formula I having the formula

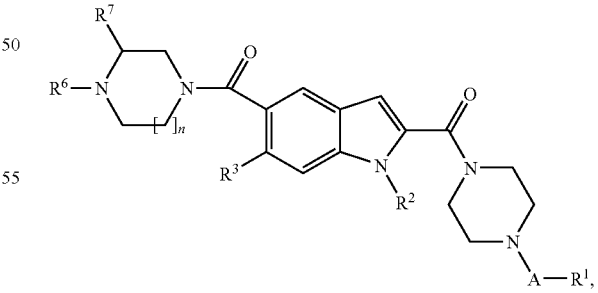

wherein A, $R^1$, $R^2$, $R^3$, $R^6$, $R^7$ and n are as defined herein before.

Within this group, the compounds of formula I are preferred, wherein $R^6$ is lower alkyl, cycloalkyl or tetrahydropyranyl, with those, wherein $R^6$ is isopropyl, being especially preferred.

Furthermore, compounds of formula I according to the invention are preferred, wherein n is 1. Compounds of formula I, wherein n is 2, are also preferred.

The present invention also includes compounds of formula I, wherein G is

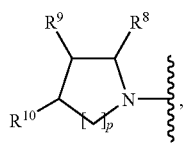

wherein p is 1 or 2;
R⁸ is hydrogen or lower heterocyclylalkyl;
R⁹ and R¹⁰ independently from each other are hydrogen or —NR¹¹R¹²; and R¹¹ and R¹² independently from each other are lower alkyl or together with the nitrogen atom to which they are attached form a 5- or 6-membered saturated heterocyclic ring optionally containing a further heteroatom of nitrogen, oxygen or sulfur,
and pharmaceutically acceptable salts thereof, meaning these are compounds of formula I having the formula

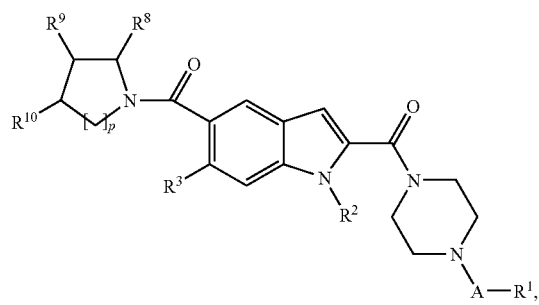

I-iv wherein A, R¹, R², R³, R⁸, R⁹, R¹⁰ and p are as defined herein before.

Preferred compounds of formula I of the present invention are the following:
[5-(4-isopropyl-piperazine-1-carbonyl)-1H-indol-2-yl]-(4-methanesulfonyl-piperazin-1-yl)-methanone,
[5-(4-isopropyl-piperazine-1-carbonyl)-1H-indol-2-yl]-[4-(piperidine-1-sulfonyl)-piperazin-1-yl]-methanone,
[1-cyclopropylmethyl-5-(4-isopropyl-piperazine-1-carbonyl)-1H-indol-2-yl]-[4-(piperidine-1-sulfonyl)-piperazin-1-yl]-methanone,
[5-(4-isopropyl-piperazine-1-carbonyl)-1-(2,2,2-trifluoro-ethyl)-1H-indol-2-yl]-[4-(piperidine-1-sulfonyl)-piperazin-1-yl]-methanone,
[1-(3-chloro-phenyl)-5-(4-isopropyl-piperazine-1-carbonyl)-1H-indol-2-yl]-(4-methanesulfonyl-piperazin-1-yl)-methanone,
[5-(4-isopropyl-piperazine-1-carbonyl)-1-(3-trifluoromethyl-phenyl)-1H-indol-2-yl]-(4-methanesulfonyl-piperazin-1-yl)-methanone,
[1-(2-chloro-pyridin-4-yl)-5-(4-isopropyl-piperazine-1-carbonyl)-1H-indol-2-yl]-(4-methanesulfonyl-piperazin-1-yl)-methanone,
[1-cyclopropylmethyl-5-(4-isopropyl-piperazine-1-carbonyl)-1H-indol-2-yl]-(4-methanesulfonyl-piperazin-1-yl)-methanone
[5-(4-isopropyl-piperazine-1-carbonyl)-1-(2,2,2-trifluoro-ethyl)-1H-indol-2-yl]-(4-methanesulfonyl-piperazin-1-yl)-methanone,
[1-(3-chloro-phenyl)-5-(4-isopropyl-piperazine-1-carbonyl)-1H-indol-2-yl]-[4-(piperidine-1-sulfonyl)-piperazin-1-yl]-methanone,
[5-(4-isopropyl-piperazine-1-carbonyl)-1-(3-trifluoromethyl-phenyl)-1H-indol-2-yl]-[4-(piperidine-1-sulfonyl)-piperazin-1-yl]-methanone,
[1-(2-chloro-pyridin-4-yl)-5-(4-isopropyl-piperazine-1-carbonyl)-1H-indol-2-yl]-[4-(piperidine-1-sulfonyl)-piperazin-1-yl]-methanone,
(4-benzenesulfonyl-piperazin-1-yl)-[5-(4-isopropyl-piperazine-1-carbonyl)-1H-indol-2-yl]-methanone,
{4-[5-(4-isopropyl-piperazine-1-carbonyl)-1H-indole-2-carbonyl]-piperazin-1-yl}-piperidin-1-yl-methanone,
[5-(4-isopropyl-piperazine-1-carbonyl)-1H-indol-2-yl]-[4-(propane-2-sulfonyl)-piperazin-1-yl]-methanone,
(4-benzenesulfonyl-piperazin-1-yl)-[1-(3-chloro-phenyl)-5-(4-isopropyl-piperazine-1-carbonyl)-1H-indol-2-yl]-methanone,
(4-benzenesulfonyl-piperazin-1-yl)-[1-(2-chloro-pyridin-4-yl)-5-(4-isopropyl-piperazine-1-carbonyl)-1H-indol-2-yl]-methanone,
[1-(3-chloro-phenyl)-5-(4-isopropyl-piperazine-1-carbonyl)-1H-indol-2-yl]-[4-(piperidine-1-carbonyl)-piperazin-1-yl]-methanone,
[1-(2-chloro-pyridin-4-yl)-5-(4-isopropyl-piperazine-1-carbonyl)-1H-indol-2-yl]-[4-(piperidine-1-carbonyl)-piperazin-1-yl]-methanone,
[1-(3-chloro-phenyl)-5-(4-isopropyl-piperazine-1-carbonyl)-1H-indol-2-yl]-[4-(propane-2-sulfonyl)-piperazin-1-yl]-methanone,
[1-(2-chloro-pyridin-4-yl)-5-(4-isopropyl-piperazine-1-carbonyl)-1H-indol-2-yl]-[4-(propane-2-sulfonyl)-piperazin-1-yl]-methanone,
(4-benzenesulfonyl-piperazin-1-yl)-[1-isopropyl-5-(4-isopropyl-piperazine-1-carbonyl)-1H-indol-2-yl]-methanone,
[1-isopropyl-5-(4-isopropyl-piperazine-1-carbonyl)-1H-indol-2-yl]-[4-(piperidine-1-carbonyl)-piperazin-1-yl]-methanone,
[1-isopropyl-5-(4-isopropyl-piperazine-1-carbonyl)-1H-indol-2-yl]-[4-(propane-2-sulfonyl)-piperazin-1-yl]-methanone,
(4-cyclopropanecarbonyl-piperazin-1-yl)-[5-(4-isopropyl-piperazine-1-carbonyl)-1H-indol-2-yl]-methanone,
(4-cyclopropanecarbonyl-piperazin-1-yl)-[1-isopropyl-5-(4-isopropyl-piperazine-1-carbonyl)-1H-indol-2-yl]-methanone,
[1-(2-chloro-pyridin-4-yl)-5-(4-isopropyl-piperazine-1-carbonyl)-1H-indol-2-yl]-(4-cyclopropanecarbonyl-piperazin-1-yl)-methanone,
[1-(6-chloro-pyridin-3-yl)-5-(4-isopropyl-piperazine-1-carbonyl)-1H-indol-2-yl]-(4-cyclopropanecarbonyl-piperazin-1-yl)-methanone,
[1-(3-chloro-phenyl)-5-(4-isopropyl-piperazine-1-carbonyl)-1H-indol-2-yl]-(4-cyclopropanecarbonyl-piperazin-1-yl)-methanone,
(4-cyclopropanecarbonyl-piperazin-1-yl)-[5-(4-isopropyl-piperazine-1-carbonyl)-1-(3-trifluoromethyl-phenyl)-1H-indol-2-yl]-methanone,
1-{4-[5-(4-isopropyl-piperazine-1-carbonyl)-1H-indole-2-carbonyl]-piperazin-1-yl}-2-methyl-propan-1-one, 4-[5-(4-isopropyl-piperazine-1-carbonyl)-1H-indole-2-carbonyl]-piperazine-1-carboxylic acid dimethylamide,
(4-cyclopropanesulfonyl-piperazine-1-yl)-[5-(4-isopropyl-piperazine-1-carbonyl)-1H-indol-2-yl]-methanone,
1-{4-[1-(2-chloro-pyridin-4-yl)-5-(4-isopropyl-piperazine-1-carbonyl)-1H-indole-2-carbonyl]-piperazin-1-yl}-2-methyl-propan-1-one,
1-{4-[1-(6-chloro-pyridin-3-yl)-5-(4-isopropyl-piperazine-1-carbonyl)-1H-indole-2-carbonyl]-piperazin-1-yl}-2-methyl-propan-1-one,
1-{4-[1-(3-chloro-phenyl)-5-(4-isopropyl-piperazine-1-carbonyl)-1H-indole-2-carbonyl]-piperazin-1-yl}-2-methyl-propan-1-one,
[1-(2-chloro-pyridin-4-yl)-5-(4-isopropyl-piperazine-1-carbonyl)-1H-indol-2-yl]-(4-cyclopropanesulfonyl-piperazin-1-yl)-methanone,
[1-(6-chloro-pyridin-3-yl)-5-(4-isopropyl-piperazine-1-carbonyl)-1H-indol-2-yl]-(4-cyclopropanesulfonyl-piperazin-1-yl)-methanone,
[1-(3-chloro-phenyl)-5-(4-isopropyl-piperazine-1-carbonyl)-1H-indol-2-yl]-(4-cyclopropanesulfonyl-piperazin-1-yl)-methanone,
4-[1-(2-chloro-pyridin-4-yl)-5-(4-isopropyl-piperazine-1-carbonyl)-1H-indole-2-carbonyl]-piperazine-1-carboxylic acid dimethylamide,
1-{4-[1-isopropyl-5-(4-isopropyl-piperazine-1-carbonyl)-1H-indole-2-carbonyl]-piperazin-1-yl}-2-methyl-propan-1-one,
(4-cyclopropanesulfonyl-piperazin-1-yl)-[1-isopropyl-5-(4-isopropyl-piperazine-1-carbonyl)-1H-indol-2-yl]-methanone,
4-[5-(4-isopropyl-piperazine-1-carbonyl)-1H-indole-2-carbonyl]-piperazine-1-carboxylic acid ethyl ester,
4-[1-isopropyl-5-(4-isopropyl-piperazine-1-carbonyl)-1H-indole-2-carbonyl]-piperazine-1-carboxylic acid dimethylamide,
4-[1-isopropyl-5-(4-isopropyl-piperazine-1-carbonyl)-1H-indole-2-carbonyl]-piperazine-1-carboxylic acid ethyl ester,
4-[1-(2-chloro-pyridin-4-yl)-5-(4-isopropyl-piperazine-1-carbonyl)-1H-indole-2-carbonyl]-piperazine-1-carboxylic acid ethyl ester,
4-[1-isopropyl-5-(4-isopropyl-[1,4]diazepane-1-carbonyl)-1H-indole-2-carbonyl]-1-carboxylic acid ethyl ester,
4-[1-isopropyl-5-(4-isopropyl-[1,4]diazepane-1-carbonyl)-1H-indole-2-carbonyl]-piperazine-1-carboxylic acid dimethylamide,
(4-methanesulfonyl-piperazin-1-yl)-{5-[4-(tetrahydro-pyran-4-yl)-[1,4]diazepane-1-carbonyl]-1H-indol-2-yl}-methanone,
4-[5-(4-cyclobutyl-[1,4]diazepane-1-carbonyl)-1H-indole-2-carbonyl]-piperazine-1-carboxylic acid ethyl ester,
[5-(4-isopropyl-[1,4]diazepane-1-carbonyl)-1H-indol-2-yl]-(4-methanesulfonyl-piperazin-1-yl)-methanone,
4-[5-(4-isopropyl-[1,4]diazepane-1-carbonyl)-1H-indole-2-carbonyl]-piperazine-1-carboxylic acid ethyl ester,
4-[5-(4-isopropyl-[1,4]diazepane-1-carbonyl)-1H-indole-2-carbonyl]-piperazine-1-carboxylic acid dimethylamide,
[1-isopropyl-5-(4-isopropyl-[1,4]diazepane-1-carbonyl)-1H-indol-2-yl]-(4-methanesulfonyl-piperazin-1-yl)-methanone,
and pharmaceutically acceptable salts thereof.

Especially preferred are the following compounds:
[1-(2-chloro-pyridin-4-yl)-5-(4-isopropyl-piperazine-1-carbonyl)-1H-indol-2-yl]-(4-methanesulfonyl-piperazin-1-yl)-methanone,
[1-(3-chloro-phenyl)-5-(4-isopropyl-piperazine-1-carbonyl)-1H-indol-2-yl]-[4-(piperidine-1-sulfonyl)-piperazin-1-yl]-methanone,
(4-benzenesulfonyl-piperazin-1-yl)-[1-(3-chloro-phenyl)-5-(4-isopropyl-piperazine-1-carbonyl)-1H-indol-2-yl]-methanone,
[1-(2-chloro-pyridin-4-yl)-5-(4-isopropyl-piperazine-1-carbonyl)-1H-indol-2-yl]-[4-(piperidine-1-carbonyl)-piperazin-1-yl]-methanone,
4-[1-isopropyl-5-(4-isopropyl-[1,4]diazepane-1-carbonyl)-1H-indole-2-carbonyl]-piperazine-1-carboxylic acid ethyl ester,
[1-isopropyl-5-(4-isopropyl-[1,4]diazepane-1-carbonyl)-1H-indol-2-yl]-(4-methanesulfonyl-piperazin-1-yl)-methanone,
and pharmaceutically acceptable salts thereof.

Furthermore, the pharmaceutically acceptable salts of the compounds of formula I and the pharmaceutically acceptable esters of the compounds of formula I individually constitute preferred embodiments of the present invention.

Compounds of formula I may form acid addition salts with acids, such as conventional pharmaceutically acceptable acids, for example hydrochloride, hydrobromide, phosphate, acetate, fumarate, maleate, salicylate, sulphate, pyruvate, citrate, lactate, mandelate, tartarate, and methanesulphonate. Preferred are the hydrochloride salts. Also solvates and hydrates of compounds of formula I and their salts form part of the present invention.

Compounds of formula I can have one or more asymmetric carbon atoms and can exist in the form of optically pure enantiomers, mixtures of enantiomers such as, for example, racemates, optically pure diastereoisomers, mixtures of diastereoisomers, diastereoisomeric racemates or mixtures of diastereoisomeric racemates. The optically active forms can be obtained for example by resolution of the racemates, by asymmetric synthesis or asymmetric chromatography (chromatography with a chiral adsorbens or eluant). The invention embraces all of these forms. It will be appreciated, that the compounds of general formula I in this invention may be derivatized at functional groups to provide derivatives which are capable of conversion back to the parent compound in vivo. Physiologically acceptable and metabolically labile derivatives, which are capable of producing the parent compounds of general formula I in vivo are also within the scope of this invention.

A further aspect of the present invention is the process for the manufacture of compounds of formula I as defined above, which process comprises a) reacting a compound of formula II

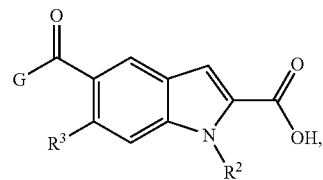

wherein G and $R^3$ are as defined herein before and $R^2$ is hydrogen, with an amine of the formula III

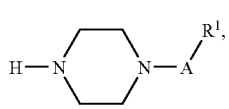

III wherein A and $R^1$ are as defined herein before, in the presence of a coupling reagent under basic conditions to obtain a compound of the formula IA

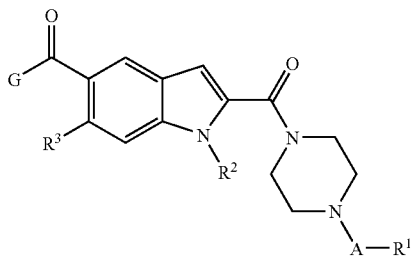

IA wherein A, $R^1$, $R^3$ and G are as defined herein before and $R^2$ is hydrogen, and optionally transferring into a compound of formula IB

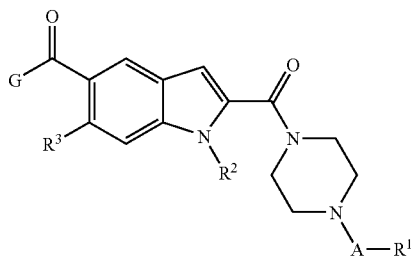

IB wherein $R^2$ is a group as defined herein before other than hydrogen, and if desired, converting the compound obtained into a pharmaceutically acceptable acid addition salt;

or, alternatively, b) reacting a compound of formula IV

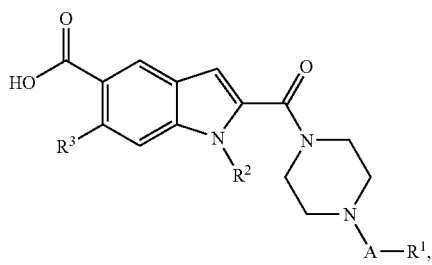

IV wherein A, $R^1$ and $R^3$ are as defined herein before and $R^2$ is hydrogen, with an amine of the formula VA or VB

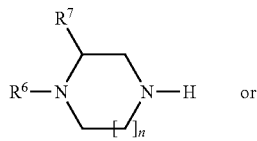

VA or

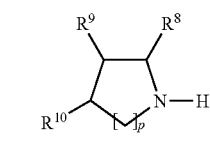

VB wherein $R^6$ to $R^{10}$, n and p are as defined herein before, in the presence of a coupling reagent under basic conditions to obtain a compound of the formula IA

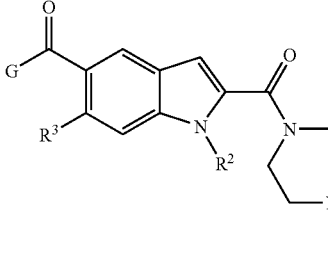

IA wherein A, $R^1$, $R^3$ and G are as defined herein before and $R^2$ is hydrogen, and optionally transferring into a compound of formula IB

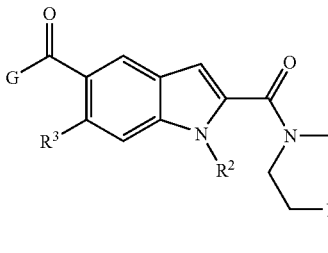

IB wherein $R^2$ is a group as defined herein before other than hydrogen, and if desired, converting the compound obtained into a pharmaceutically acceptable acid addition salt.

Appropriate coupling reagents are for example N,N-carbonyldiimidazole (CDI) or 1-hydroxy-1,2,3-benzotriazole (HOBT). The reaction is carried out in a suitable solvent such as for example dimethylformamide (DMF) or dioxane in the presence of an appropriate base. Preferred is a base such as triethylamine or diisopropylethylamine.

Transferring into a compound of formula IB means treating the compound of formula IA with a suitable base in a suitable solvent under anhydrous conditions (e.g. sodium hydride in DMF) and reacting the intermediate anion with an alkylating or acylating agent $R^2$—X, wherein X signifies a leaving group such as e.g. iodide, bromide, methanesulfonate or chloride, to obtain a compound of formula IB wherein $R^2$ signifies lower alkyl, lower hydroxyalkyl, lower alkoxyalkyl, lower halogenalkyl, lower cycloalkylalkyl, lower alkanoyl, lower cyanoalkyl, lower alkylsulfonyl or phenylsulfonyl, or alternatively, transferring into a compound of formula IB means reacting a compound of formula IA with an optionally substituted phenylboronic acid using an appropriate catalyst (e.g. copper(II) acetate) and base (e.g. pyridine) in a suitable solvent like, e.g. dichloromethane, to obtain a compounds of formula IB where $R^3$ signifies a phenyl or a substituted phenyl group.

In more detail, the compounds of formula I can be manufactured by the methods given below, by the methods given in the examples or by analogous methods. The substituents and indices used in the following description of the processes have the significance given herein before unless indicated to the contrary. The reaction sequence is not limited to the one displayed in scheme 1, however, depending on the starting materials and their respective reactivity the sequence of reaction steps can be freely altered. Starting materials are either commercially available or can be prepared by methods analogous to the methods given below, by methods described in references cited in the description or in the examples, or by methods known in the art.

Compounds of the general formula IA and IB can be prepared according to scheme 1 by a process whereby the 2-carbethoxyindole-5-carboxylic acid of formula A (prepared according to, e.g. Lindwall, H. G.; Mantell, G. J.; J. Org. Chem. 1953, 18, 345) is first reacted with an amine of formula I (either commercially available or accessible by methods described in references or by methods known in the art) to give intermediate B. The coupling of carboxylic acids with amines (either commercially available or accessible by methods described in references or by methods known in the art) is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents such as, e.g. N,N-carbonyldiimidazole (CDI), 1-hydroxy-1,2,3-benzotriazole (HOBT) or O-benzotriazol-1-yl-N,N,N,N-tetramethyluronium tetrafluoroborate (TBTU) in a suitable solvent such as, e.g. dimethylformamide (DMF) or dioxane in the presence of an appropriate base (e.g. triethylamine or diisopropylethylamine). The ester functionality in intermediates B is cleaved under basic (e.g. with lithium hydroxide in polar solvents such as, e.g. methanol, water or THF or mixtures of said solvents) or under acidic conditions (e.g. using concentrated hydrochloric acid in THF or other suitable solvent). Subsequent transformation of the resulting either lithium or hydrochloride salt of intermediate C to compounds of the general formula IA can be accomplished by using piperazine derivatives II (either commercially available or accessible by methods described in references, e.g. S. Scapecchi et al., Bioorg. Med. Chem. 2004, 12, 71-85, or by methods known in the art) and applying the afore-mentioned methods.

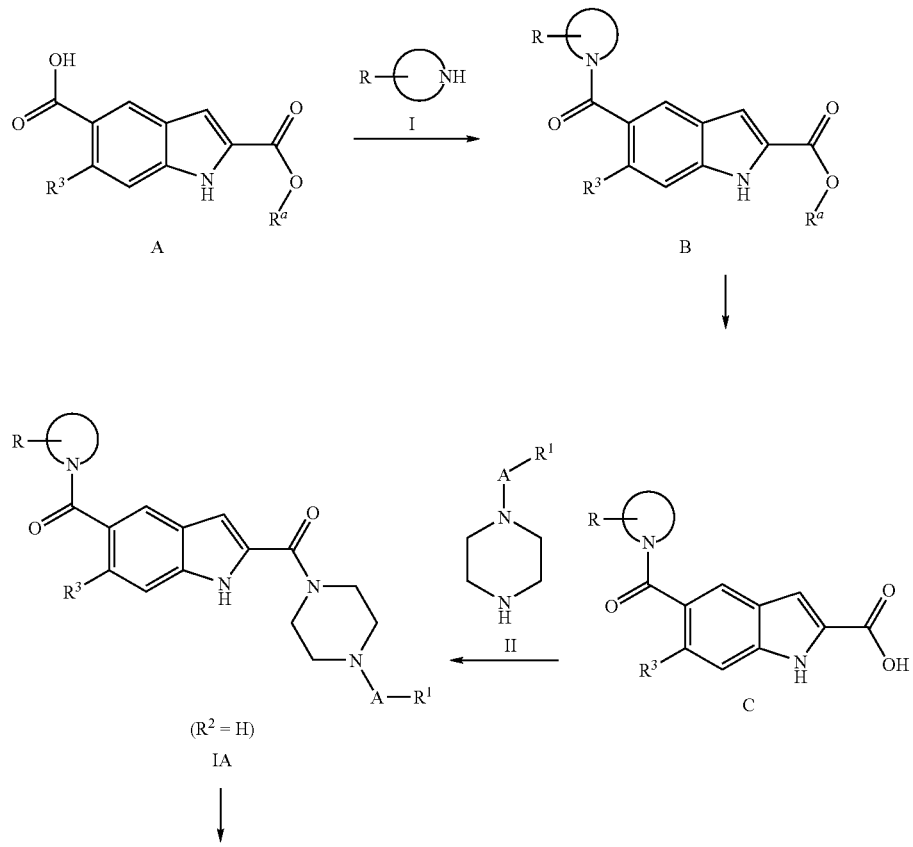

Scheme 1

-continued

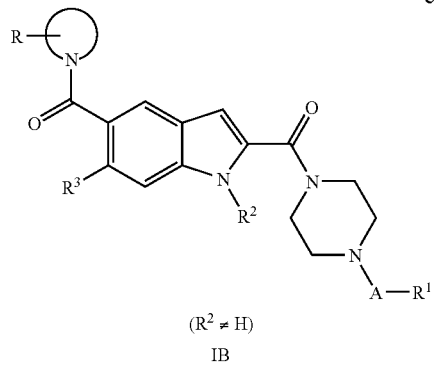

(R² ≠ H)
IB

R = R⁶-R¹⁰ as defined before

Intermediates of formula IB can be obtained for example through treatment of intermediates of formula IA with a suitable base in a suitable solvent under anhydrous conditions (e.g. sodium hydride in DMF) and reacting the intermediate anion with an alkylating or acylating agent R²—X such as, e.g. methyl iodide, 2-bromopropane, 2,2,2-trifluoroethyl-methanesulfonate, methanesulfonyl- or phenylsulfonylchloride. In those cases R² signifies a methyl, trifluoromethyl, isopropyl or an alkyl- or arylsulfonyl group and X signifies a leaving group such as, e.g. iodide, bromide, methanesulfonate or chloride. Compounds of formula IB where R² signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula IA are reacted with an optionally substituted phenylboronic acid using an appropriate catalyst (e.g. copper(II) acetate) and base (e.g. pyridine) in a suitable solvent such as, e.g. dichloromethane. $R^a$ in scheme 1 is an alkyl group, preferably a lower alkyl group, preferably methyl or ethyl.

Scheme 2

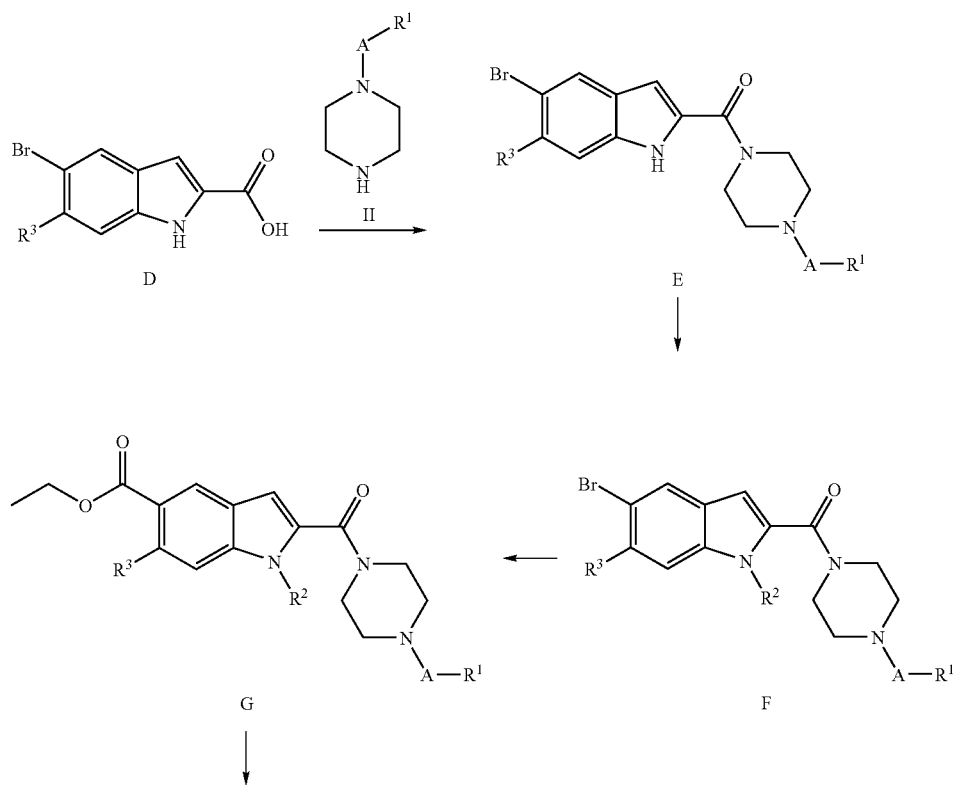

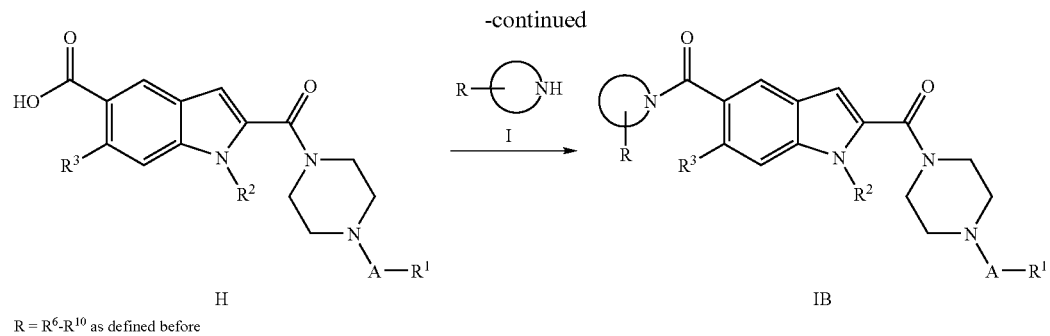

R = R⁶-R¹⁰ as defined before

Compounds of general formula IB can be prepared according to scheme 2 by a process involving the reaction of 5-bromoindole-2-carboxylic acid (commercially available) with piperazine derivatives of formula II (either commercially available or accessible by methods described in references, e.g. S. Scapecchi et al., Bioorg. Med. Chem. 2004, 12, 71-85, or by methods known in the art) to give intermediates E. The coupling of carboxylic acids with amines is widely described in literature (e.g. Comprehensive Organic Transformations: A Guide to Functional Group Preparations, 2nd Edition, Richard C. Larock. John Wiley & Sons, New York, N.Y. 1999) and can be accomplished by employing the usage of coupling reagents (e.g. N,N-carbonyldiimidazole). Intermediates of formula F can be obtained for example through treatment of intermediates of formula E with a suitable base in a suitable solvent under anhydrous conditions (e.g. sodium hydride in tetrahydrofuran) and reacting the intermediate anion with an alkylating or acylating agent R²—X such as, e.g. methyl iodide, 2-bromopropane, 2,2,2-trifluoroethyl-methanesulfonate, methanesulfonyl- or phenylsulfonylchloride. In those cases R² signifies a methyl, trifluoromethyl, isopropyl or an alkyl- or arylsulfonyl group and X signifies a leaving group such as, e.g. iodide, bromide, methanesulfonate or chloride. Compounds of formula F where R² signifies a phenyl or a substituted phenyl group can be synthesized by processes known to those skilled in the art and described in literature (e.g. W. W. K. R. Mederski et. al, Tetrahedron, 1999, 55, 12757). For example, intermediates of formula E are reacted with an optionally substituted phenylboronic acid using an appropriate catalyst (e.g. copper(II) acetate) and base (e.g. pyridine) in a suitable solvent (e.g. dichloromethane).

Intermediates of formula G can be obtained for example through treatment of intermediates of formula F with a palladium source (e.g. palladium acetate) and suitable ligand (e.g. 1,3-(diphenylphosphino)ferrocene) in a suitable solvent or solvent mixture (e.g. 1:1 v:v dimethylsulfoxide/ethanol) under carbon monoxide atmosphere (at, e.g. 1 atmosphere) by processes known to those skilled in the art and described in literature (e.g. Kumar, K. Org. Letters 2004, 6, 4).

The ester functionality in intermediates G is cleaved under basic (e.g. with lithium hydroxide in polar solvents such as, e.g. methanol, water or THF or mixtures of said solvents) or under acidic conditions (e.g. using concentrated hydrochloric acid in THF) and subsequent transformation of the resulting either lithium salt or salt-free intermediate H to compounds of the general formula IB applying the afore-mentioned methods.

Scheme 3

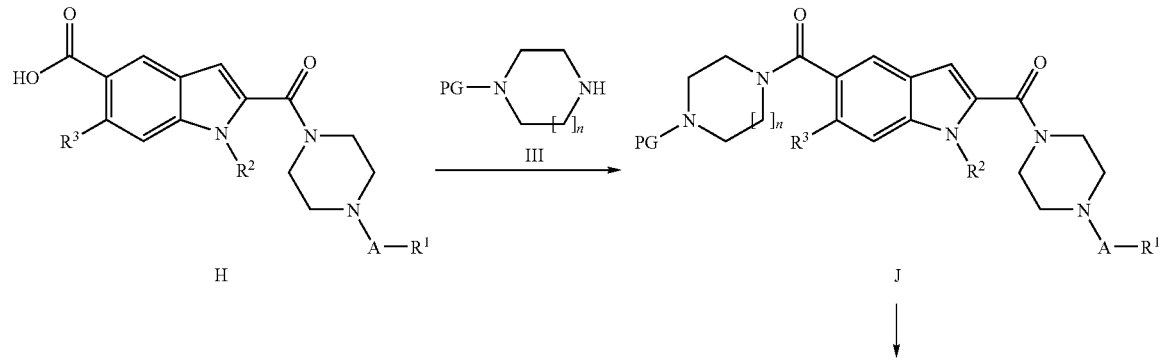

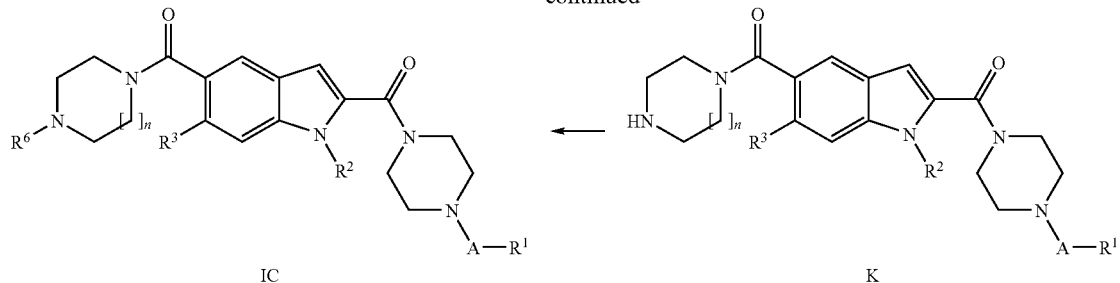

In cases of substituents G1 where the substituent $R^6$ is not already present in the corresponding piperidine or homopiperidine substituent III, $R^6$ can be introduced as exemplified in scheme 3. Amide coupling of intermediates H with protected (e.g. with a tert-butoxycarbonyl protective group) and optionally substituted piperidines or homopiperidines leads to intermediates J, which in turn can be deprotected (e.g. a tert-butoxycarbonyl group by using, e.g. trifluoroacetic acid in dichloromethane) to give intermediates K. Alkylation of the free amine functionality in intermediates K by employing methods described in references or by methods known in the art such as, e.g. reductive amination (e.g. F. Zaragoza, et. al, J. Med. Chem. 2004, 47, 2833) gives compounds of the general formula IC.

Alternately, compounds of general formula I may be prepared as shown in Scheme 4. Amide coupling of intermediates A with protected (e.g. with a tert-butoxycarbonyl protective group) and optionally substituted piperidines or homopiperidines leads to intermediates L. The ester functionality in intermediates L is cleaved under basic (e.g. with lithium hydroxide in polar solvents such as, e.g. methanol, water or THF or mixtures of said solvents) or under acidic conditions (e.g. using concentrated hydrochloric acid in THF). Subsequent transformation of the resulting either lithium or hydrochloride salt of intermediate M to compounds of the general formula N can be accomplished by using piperazine derivatives II (either commercially available or accessible by methods described in references, e.g. S. Scapecchi et al., Bioorg. Med. Chem. 2004, 12, 71-85, or by methods known in the art) and applying the afore-mentioned methods.

Scheme 4

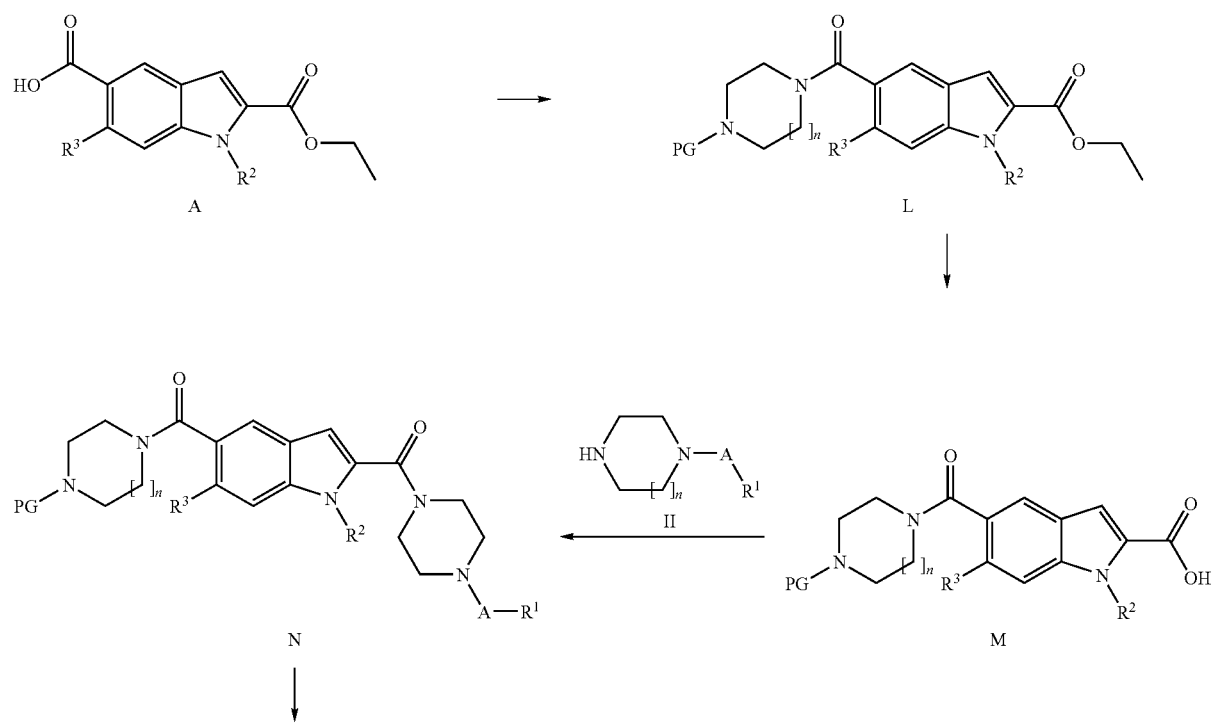

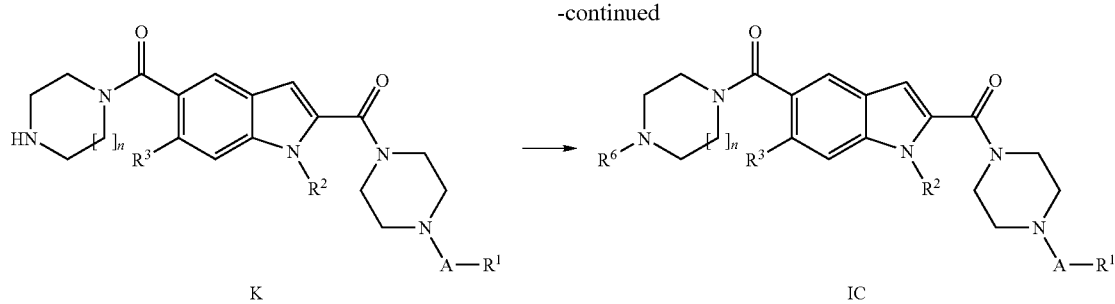

K → IC

Intermediates N can be deprotected (e.g. a tert-butoxycarbonyl group by using, e.g. trifluoroacetic acid in dichloromethane, or hydrogen chloride in a suitable solvent such as ethyl acetate or methanol) to give intermediates K. Alkylation of the free amine functionality in intermediates K by employing methods described in references or by methods known in the art such as, e.g. reductive amination (e.g. F. Zaragoza, et. al, J. Med. Chem. 2004, 47, 2833) gives compounds of the general formula IC.

The compounds of formula I can contain several asymmetric centres and can be present in the form of optically pure enantiomers, mixtures of enantiomers such as, e.g. racemates, optically pure diastereomers, mixtures of diastereomers, diastereomeric racemates or mixtures of diastereomeric racemates. The optically active forms can be obtained for example by resolution of the racemates, by asymmetric synthesis or asymmetric chromatography (chromatography with a chiral adsorbent or eluant).

As described above, the compounds of formula I of the present invention can be used as medicaments for the treatment and/or prevention of diseases which are associated with the modulation of H3 receptors.

In this context, the expression 'diseases associated with the modulation of H3 receptors' means diseases which can be treated and/or prevented by modulation of H3 receptors. Such diseases encompass, but are not limited to, obesity, metabolic syndrome (syndrome X), neurological diseases including Alzheimer's disease, dementia, age-related memory dysfunction, mild cognitive impairment, cognitive deficit, attention deficit hyperactivity disorder, epilepsy, neuropathic pain, inflammatory pain, migraine, Parkinson's disease, multiple sclerosis, stroke, dizziness, schizophrenia, depression, addiction, motion sickness and sleep disorders including narcolepsy, and other diseases including asthma, allergy, allergy-induced airway responses, congestion, chronic obstructive pulmonary disease and gastro-intestinal disorders.

In a preferable aspect, the expression 'diseases associated with modulation of H3 receptors' relates to obesity, metabolic syndrome (syndrome X), and other eating disorders, with obesity being especially preferred.

The invention therefore also relates to pharmaceutical compositions comprising a compound as defined above and a pharmaceutically acceptable carrier and/or adjuvant.

Further, the invention relates to compounds as defined above for use as therapeutically active substances, particularly as therapeutic active substances for the treatment and/or prevention of diseases which are associated with the modulation of H3 receptors.

In another embodiment, the invention relates to a method for the treatment and/or prevention of diseases which are associated with the modulation of H3 receptors, which method comprises administering a therapeutically active amount of a compound of formula I to a human being or animal. A method for the treatment and/or prevention of obesity is preferred.

The invention further relates to the use of compounds of formula I as defined above for the treatment and/or prevention of diseases which are associated with the modulation of H3 receptors.

In addition, the invention relates to the use of compounds of formula I as defined above for the preparation of pharmaceutical compositions for the treatment and/or prevention of diseases which are associated with the modulation of H3 receptors. The use of compounds of formula I as defined above for the preparation of pharmaceutical compositions for the treatment and/or prevention of obesity is preferred.

Furthermore, the present invention relates to the use of a compound of formula I for the manufacture of a pharmaceutical composition for the treatment and prevention of obesity in a patient who is also receiving treatment with a lipase inhibitor and particularly, wherein the lipase inhibitor is orlistat.

It is a further preferred object of the present invention to provide a method for the treatment or prevention of obesity and obesity related disorders which comprises administration of a therapeutically effective amount of a compound according to formula I in combination or association with a therapeutically effective amount of other drugs for the treatment of obesity or eating disorders so that together they give effective relief. Suitable other drugs include, but are not limited to, anorectic agents, lipase inhibitors, selective serotonin reuptake inhibitors (SSRI) and agents that stimulate metabolism of body fat. Combinations or associations of the above agents may be encompassing separate, sequential or simultaneous administration.

The term "lipase inhibitor" refers to compounds which are capable of inhibiting the action of lipases, for example gastric and pancreatic lipases. For example orlistat and lipstatin as described in U.S. Pat. No. 4,598,089 are potent inhibitor of lipases. Lipstatin is a natural product of microbial origin, and orlistat is the result of a hydrogenation of lipstatin. Other lipase inhibitors include a class of compound commonly referred to as panclicins. Panclicins are analogues of orlistat (Mutoh et al, 1994). The term "lipase inhibitor" refers also to polymer bound lipase inhibitors for example described in International Patent Application WO 99/34786 (Geltex Pharmaceuticals Inc.). These polymers are characterized in that they have been substituted with one or more groups that inhibit lipases. The term "lipase inhibitor" also comprises pharmaceutically acceptable salts of these compounds. The term "lipase inhibitor" preferably refers to tetrahydrolipstatin. Administration of a therapeutically effective amount of a compound according to formula I in combination or association with a therapeutically effective amount of tetrahydrolipstatin is especially preferred.

Tetrahydrolipstatin (orlistat) is a known compound useful for the control or prevention of obesity and hyperlipidemia. See, U.S. Pat. No. 4,598,089, issued Jul. 1, 1986, which also discloses processes for making orlistat and U.S. Pat. No. 6,004,996, which discloses appropriate pharmaceutical compositions. Further suitable pharmaceutical compositions are described for example in International Patent Applications WO 00/09122 and WO 00/09123. Additional processes for the preparation of orlistat are disclosed in European Patent Applications Publication Nos. 0 185 359, 0 189 577, 0 443 449, and 0 524 495.

Suitable anorectic agents of use in combination with a compound of the present invention include, but are not limited to, APD356, aminorex, amphechloral, amphetamine, axokine, benzphetamine, bupropion, chlorphentermine, clobenzorex, cloforex, clominorex, clortermine, CP945598, cyclexedrine, CYT009-GhrQb, dexfenfluramine, dextroamphetamine, diethylpropion, diphemethoxidine, N-ethylamphetamine, fenbutrazate, fenfluramine, fenisorex, fenproporex, fludorex, fluminorex, furfurylmethylamphetamine, levamfetamine, levophacetoperane, mazindol, mefenorex, metamfepramone, methamphetamine, metreleptin, norpseudoephedrine, pentorex, phendimetrazine, phenmetrazine, phentermine, phenylpropanolamine, picilorex, rimonabant, sibutramine, SLV319, SNAP 7941, SR147778 (Surinabant), steroidal plant extract (e.g. P57) and TM30338 and pharmaceutically acceptable salts thereof.

Most preferable anorectic agents are sibutramine, rimonabant and phentermine. Suitable selective serotonin reuptake inhibitors of use in combination with a compound of the present invention include: fluoxetine, fluvoxamine, paroxetine and sertraline, and pharmaceutically acceptable salts thereof.

Suitable agents that stimulate metabolism of body fat include, but are not limited to, growth hormone agonist (e.g. AOD-9604).

The use of a compound of formula I in the manufacture of a pharmaceutical composition for the treatment and prevention of obesity in a patient who is also receiving treatment with a compound selected from the group consisting of a lipase inhibitor, an anorectic agent, a selective serotonin reuptake inhibitor, and an agent that stimulates metabolism of body fat, is also an object of the present invention.

The use of a compound of formula I in the manufacture of a pharmaceutical composition for the treatment and prevention of obesity in a patient who is also receiving treatment with a lipase inhibitor, preferably with tetrahydrolipstatin, is also an object of the present invention.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of a lipase inhibitor, particularly, wherein the lipase inhibitor is tetrahydrolipstatin. Also an object of the invention is the method as described above for the simultaneous, separate or sequential administration of a compound according to formula I and a lipase inhibitor, particularly tetrahydrolipstatin.

It is a further preferred object to provide a method of treatment or prevention of Type II diabetes (non-insulin dependent diabetes mellitus (NIDDM)) in a human which comprises administration of a therapeutically effective amount of a compound according to formula I in combination or association with a therapeutically effective amount of an anti-diabetic agent.

The term "anti-diabetic agent" refers to compounds selected from the group consisting of 1) PPARγ agonists such as pioglitazone (actos) or rosiglitazone (avandia), and the like; 2) biguanides such as metformin (glucophage), and the like; 3) sulfonylureas such as glibenclamide, glimepiride (amaryl), glipizide (glucotrol), glyburide (DiaBeta), and the like; 4) nonsulfonylureas such as nateglinide (starlix), repaglimide (prandin), and the like; 5) PPARα/γ agonists such as GW-2331, and the like 6) DPP-IV-inhibitors such as LAF-237 (vildagliptin), MK-0431, BMS-477118 (saxagliptin) or GSK23A and the like; 7) Glucokinase activators such as the compounds disclosed in e.g. WO 00/58293 A1, and the like; 8) α-Glucosidase inhibitors such as acarbose (precose) or miglitol (glyset), and the like.

Also an object of the invention is the method as described above for the simultaneous, separate or sequential administration of a compound according to formula I and a therapeutically effective amount of an anti-diabetic agent.

The use of a compound of formula I in the manufacture of a pharmaceutical composition for the treatment and prevention of Type II diabetes in a patient who is also receiving treatment with an anti-diabetic agent is also an object of the present invention.

It is a further preferred object to provide a method of treatment or prevention of dyslipidemias in a human which comprises administration of a therapeutically effective amount of a compound according to formula I in combination or association with a therapeutically effective amount of a lipid lowering agent.

The term "lipid lowering agent" refers to compounds selected from the group consisting of 1) bile acid sequestrants such as cholestyramine (questran), colestipol (colestid), and the like; 2) HMG-CoA reductase inhibitors such as atorvastatin (lipitor), cerivastatin (baycol), fluvastatin (lescol), pravastatin (pravachol), simvastatin (zocor) and the like; 3) cholesterol absorption inhibitors such as ezetimibe, and the like; 4) CETP inhibitors such as torcetrapib, JTT 705, and the like; 5) PPARα-agonists such as beclofibrate, gemfibrozil (lopid), fenofibrate (lipidil), bezafibrate (bezalip), and the like; 6) lipoprotein synthesis inhibitors such as niacin, and the like; and 7) niacin receptor agonists such as nicotinic acid, and the like.

Also an object of the invention is the method as described above for the simultaneous, separate or sequential administration of a compound according to formula I and a therapeutically effective amount of a lipid lowering agent.

The use of a compound of formula I in the manufacture of a pharmaceutical composition for the treatment and prevention of dyslipidemias in a patient who is also receiving treatment with a lipid lowering agent, is also an object of the present invention.

It is a further preferred object to provide a method of treatment or prevention of hypertension in a human which comprises administration of a therapeutically effective amount of a compound according to formula I in combination or association with a therapeutically effective amount of an anti-hypertensive agent.

The term "anti-hypertensive agent" or "blood-pressure lowering agent" refers to compounds selected from the group consisting of 1) Angiotensin-converting Enzyme (ACE) Inhibitors including benazepril (lotensin), captopril (capoten), enalapril (vasotec), fosinopril (monopril), lisinopril (prinivil, zestril), moexipril (univasc), perindopril (coversum), quinapril (accupril), ramipril (altace), trandolapril (mavik), and the like; 2) Angiotensin II Receptor Antagonists including candesartan (atacand), eprosartan (teveten), irbesartan (avapro), losartan (cozaar), telmisartan (micadisc), valsartan (diovan), and the like; 3) Adrenergic Blockers (peripheral or central) such as the beta-adrenergic blockers including acebutolol (sectrol), atenolol (tenormin), betaxolol (kerlone), bisoprolol (zebeta), carteolol (cartrol), metoprolol (lopressor; toprol-XL), nadolol (corgard), penbutolol (levatol), pindolol (visken), propranolol (inderal), timolol (blockadren) and the like; alpha/beta adrenergic blockers including carvedilol (coreg), labetalol (normodyne), and the like; alpha-1 adrenergic blockers including prazosin (minipress), doxazosin (cardura), terazosin (hytrin), phenoxybenzamine (dibenzyline), and the like; peripheral adrenergic-neuronal blockers including guanadrel (hylorel), guanethidine (ismelin), reserpine (serpasil), and the like; alpha-2 adrenergic blockers including a-methyldopa (aldomet), clonidine (catapres), guanabenz (wytensin), guanfacine (tenex), and the like; 4) Blood Vessel Dilators (Vasodilators) including hydralazine (apresoline), minoxidil (lonitren), clonidine (catapres), and the like; 5) Calcium Channel Blockers including amlodipine (norvasc), felodipine (plendil), isradipine (dynacirc), nicardipine (cardine sr), nifedipine (procardia, adalat), nisoldipine (sular), diltiazem (cardizem), verapamil (isoptil), and the like; 6) Diuretics such as thiazides and thiazides-like agents, including hydrochlorothiazide (hydrodiuril, microzide), chlorothiazide (diuril), chlorthalidone (hygroton), indapamide (lozol), metolazone (mykrox), and the like; loop diuretics, such as bumetanide (bumex) and furosemide (lasix), ethacrynic acid (edecrin), torsemide (demadex), and the like; potassium-sparing diuretics including amiloride (midamor), triamterene (dyrenium), spironolactone (aldactone), and the tiamenidine (symcor) and the like; 7) Tyrosine Hydroxylase Inhibitors, including metyrosine (demser), and the like; 8) Neutral Endopeptidase Inhibitors, including BMS-186716 (omapatrilat), UK-79300 (candoxatril), ecadotril (sinorphan), BP-1137 (fasidotril), UK-79300 (sampatrilat) and the like; and 9) Endothelin Antagonists including tezosentan, A308165, and the like. Also an object of the invention is the method as described above for the simultaneous, separate or sequential administration of a compound according to formula I and a therapeutically effective amount of an anti-hypertensive agent.

The use of a compound of formula I in the manufacture of a pharmaceutical composition for the treatment and prevention of hypertension in a patient who is also receiving treatment with an anti-hypertensive agent, is also an object of the present invention.

As described above, the compounds of formula I and their pharmaceutically acceptable salts possess valuable pharmacological properties. Specifically, it has been found that the compounds of the present invention are good histamine 3 receptor (H3R) antagonists and/or inverse agonists.

The following test was carried out in order to determine the activity of the compounds of formula I.

Binding Assay with $^3$H-(R)α-methylhistamine

Saturation binding experiments were performed using HR3-CHO membranes prepared as described in Takahashi, K, Tokita, S., Kotani, H. (2003) J. Pharmacol. Exp. Therapeutics 307, 213-218.

An appropriate amount of membrane (60 to 80 µg protein/well) was incubated with increasing concentrations of $^3$H(R) α-Methylhistamine di-hydrochloride (0.10 to 10 nM). Non specific binding was determined using a 200 fold excess of cold (R)α-Methylhistamine dihydrobromide (500 nM final concentration). The incubation was carried out at room temperature (in deep-well plates shaking for three hours). The final volume in each well was 250 µl. The incubation was followed by rapid filtration on GF/B filters (pre-soaked with 100 µl of 0.5% PEI in Tris 50 mM shaking at 200 rpm for two hours). The filtration was made using a cell-harvester and the filter plates were then washed five times with ice cold washing buffer containing 0.5 M NaCl. After harvesting, the plates were dried at 55° C. for 60 min, then we added scintillation fluid (Microscint 40, 40 microl in each well) and the amount of radioactivity on the filter was determined in Packard topcounter after shaking the plates for two hours at 200 rpm at room temperature.

Binding Buffer: 50 mM Tris-HCl pH 7.4 and 5 mM MgCl$_2$× 6H$_2$O pH 7.4. Washing Buffer: 50 mM Tris-HCl pH 7.4 and 5 mM MgCl$_2$×6H$_2$O and 0.5 M NaCl pH 7.4.

Indirect measurement of affinity of H3R inverse agonists: twelve increasing concentrations (ranging from 10 µM to 0.3 nM) of the selected compounds were always tested in competition binding experiments using membrane of the human H3R—CHO cell line. An appropriate amount of protein, e.g. approximately 500 cpm binding of RAMH at Kd, were incubated for 1 hour at room temperature in 250 µl final volume in 96-well plates in presence of $^3$H(R)α-methylhistamine (1 nM final concentration=Kd). Non-specific binding was determined using a 200 fold excess of cold (R)α-methylhistamine dihydrobromide.

All compounds were tested at a single concentration in duplicate. Compounds that showed an inhibition of [$^3$H]-RAMH by more than 50% were tested again to determine IC$_{50}$ in a serial dilution experiment, meaning concentrations were spanning 10 points starting from 4.6×10$^{-6}$ M to 1.0× 10$^{-9}$ M. The dilution factor was 1/2.15 for the whole series. The concentration at which 50% inhibition of the radioligand $^3$H(R)α-methylhistamine is obtained (the IC$_{50}$) is determined from the linear regression of a plot of the logarithm of the concentration versus percent inhibition measured for the different concentrations. Ki's were calculated from IC$_{50}$ based on Cheng-Prusoff equation (Cheng, Y, Prusoff, W H (1973) Biochem Pharmacol 22, 3099-3108): $K_i$=IC$_{50}$/[1+D/Kd] wherein D is the concentration of the radioligand and Kd is the binding constant for the radioligand binding to the receptor under the conditions used in the competition experiment.

The compounds of the present invention exhibit $K_i$ values within the range of about 1 nM to about 1000 nM, preferably of about 1 nM to about 100 nM, and more preferably of about 1 nM to about 30 nM. The following table shows measured values for some selected compounds of the present invention.

|  | $K_i$ (nM) |
| --- | --- |
| Example 7 | 11.7 |
| Example 17 | 5.7 |
| Example 19 | 7.5 |

Demonstration of additional biological activities of the compounds of the present invention may be accomplished through in vitro, ex vivo, and in vivo assays that are well known in the art. For example, to demonstrate the efficacy of a pharmaceutical agent for the treatment of obesity-related disorders such as diabetes, Syndrome X, or atherosclerotic disease and related disorders such as hypertriglyceridemia and hypercholesteremia, the following assays may be used.

Method for Measuring Blood Glucose Levels db/db mice (obtained from Jackson Laboratories, Bar Harbor, Me.) are bled (by either eye or tail vein) and grouped according to equivalent mean blood glucose levels. They are dosed orally (by gavage in a pharmaceutically acceptable vehicle) with the test compound once daily for 7 to 14 days. At this point, the animals are bled again by eye or tail vein and blood glucose levels are determined.

Method for Measuring Triglyceride Levels hApoAl mice (obtained from Jackson Laboratories, Bar Harbor, Me.) are bled (by either eye or tail vein) and grouped according to equivalent mean serum triglyceride levels. They are dosed orally (by gavage in a pharmaceutically acceptable vehicle) with the test compound once daily for 7 to 14 days. The animals are then bled again by eye or tail vein, and serum triglyceride levels are determined.

Method for Measuring HDL-Cholesterol Levels

To determine plasma HDL-cholesterol levels, hApoAl mice are bled and grouped with equivalent mean plasma HDL-cholesterol levels. The mice are orally dosed once daily with vehicle or test compound for 7 to 14 days, and then bled on the following day. Plasma is analyzed for HDL-cholesterol.

The compounds of formula I and their pharmaceutically acceptable salts and esters can be used as medicaments, e.g. in the form of pharmaceutical preparations for enteral, parenteral or topical administration. They can be administered, for example, perorally, e.g. in the form of tablets, coated tablets, dragees, hard and soft gelatine capsules, solutions, emulsions or suspensions, rectally, e.g. in the form of suppositories, parenterally, e.g. in the form of injection solutions or infusion solutions, or topically, e.g. in the form of ointments, creams or oils.

The production of the pharmaceutical preparations can be effected in a manner which will be familiar to any person skilled in the art by bringing the described compounds of formula I and their pharmaceutically acceptable, into a galenical administration form together with suitable, non-toxic, inert, therapeutically compatible solid or liquid carrier materials and, if desired, usual pharmaceutical adjuvants.

Suitable carrier materials are not only inorganic carrier materials, but also organic carrier materials. Thus, for example, lactose, corn starch or derivatives thereof, talc, stearic acid or its salts can be used as carrier materials for tablets, coated tablets, dragees and hard gelatine capsules. Suitable carrier materials for soft gelatine capsules are, for example, vegetable oils, waxes, fats and semi-solid and liquid polyols (depending on the nature of the active ingredient no carriers are, however, required in the case of soft gelatine capsules). Suitable carrier materials for the production of solutions and syrups are, for example, water, polyols, sucrose, invert sugar and the like. Suitable carrier materials for injection solutions are, for example, water, alcohols, polyols, glycerol and vegetable oils. Suitable carrier materials for suppositories are, for example, natural or hardened oils, waxes, fats and semi-liquid or liquid polyols. Suitable carrier materials for topical preparations are glycerides, semi-synthetic and synthetic glycerides, hydrogenated oils, liquid waxes, liquid paraffins, liquid fatty alcohols, sterols, polyethylene glycols and cellulose derivatives.

Usual stabilizers, preservatives, wetting and emulsifying agents, consistency-improving agents, flavor-improving agents, salts for varying the osmotic pressure, buffer substances, solubilizers, colorants and masking agents and antioxidants come into consideration as pharmaceutical adjuvants.

The dosage of the compounds of formula I can vary within wide limits depending on the disease to be controlled, the age and the individual condition of the patient and the mode of administration, and will, of course, be fitted to the individual requirements in each particular case. For adult patients a daily dosage of about 1 mg to about 1000 mg, especially about 1 mg to about 100 mg, comes into consideration. Depending on the dosage it is convenient to administer the daily dosage in several dosage units.

The pharmaceutical preparations conveniently contain about 0.1-500 mg, preferably 0.5-100 mg, of a compound of formula I.

The following examples serve to illustrate the present invention in more detail. They are, however, not intended to limit its scope in any manner. MS=mass spectrometry.

EXAMPLES

Example 1

[5-(4-Isopropyl-piperazine-1-carbonyl)-1H-indol-2-yl]-(4-methanesulfonyl-piperazin-1-yl)-methanone To a solution of 1.70 g (4.8 mmol) 5-(4-isopropyl-piperazine-1-carbonyl)-1H-indole-2-carboxylic acid hydrochloride in 17 mL N,N-dimethylformamide, were added 1.94 g (6.0 mmol) O-(benzotriazol-1-yl)-N,N,N',N'-tetramethyluronium tetrafluoroborate, 1.0 g (6.0 mmol) 1-methylsulfonyl-piperazine and 4.1 mL (3.1 g, 24.0 mmol) N,N-diisopropylethylamine. After 2 h the solution was poured into 10% aqueous ammonium chloride solution, the phases were separated and the aqueous phase was extracted ten times with ethyl acetate. The combined organic layers were washed three times with water, brine, dried over magnesium sulfate, filtered and evaporated. The residue was flash-chromatographed twice on silica gel with dichloromethane:methanol (9:1 v/v) as eluant to give 1.45 g (65%) of the desired compound as a light-brown foam. MS (ISP): 462.1 $(M+H)^+$.

Intermediates a) 5-(4-Isopropyl-piperazine-1-carbonyl)-1H-indole-2-carboxylic acid ethyl ester To a solution of 5.0 g (21.4 mmol) 1H-indole-2,5-dicarboxylic acid 2-ethyl ester (prepared according to J. Org. Chem. 1953, 18, 345-57) in 50 mL N,N-dimethylformamide, were added 8.6 g (26.8 mmol) O-(benzotriazol-1-yl)-N,N,N',N'-tetramethyluronium tetrafluoroborate. After 10 min., 3.44 g (26.8 mmol) 1-isopropylpiperazine and 18.3 mL (13.9 g, 107.4 mmol) N,N-diisopropylethylamine were added. After 45 min. the reaction mixture was poured into saturated aqueous sodium bicarbonate solution and extracted three times with ethyl acetate. The combined organic layers were washed three times with water, brine, dried over magnesium sulfate, filtered and evaporated. The residue was flash-chromatographed on silica gel with dichloromethane:methanol:ammonia (9:1:0.1 v/v) and ethyl acetate:methanol (9:1) as eluant to give 5.5 g (74%) of the desired compound as a light yellow solid. MS (ISP): 344.3 $(M+H)^+$.

b) 5-(4-Isopropyl-piperazine-1-carbonyl)-1H-indole-2-carboxylic acid hydrochloride To a solution of 2.8 g (8.1 mmol) 5-(4-isopropyl-piperazine-1-carbonyl)-1H-indole-2-carboxylic acid ethyl ester in 110 mL tetrahydrofuran, was added 0.24 g (10.1 mmol) lithium hydroxide monohydrate, followed by 55 mL water. The resulting yellow solution was stirred under reflux for 1.75 hours. The organic solvent was evaporated and the remaining turbid aqueous residue was treated with 4 M hydrochloric acid until a pH of 2 was reached. The volatile components were evaporated to dryness to afford 3 g of the desired compound as the hydrochloride salt containing lithium chloride. This material was used without further purification. MS (ISP): 316.1 (M+H)$^+$.

Example 2

[5-(4-Isopropyl-piperazine-1-carbonyl)-1H-indol-2-yl]-[4-(piperidine-1-sulfonyl)-piperazin-1-yl]-methanone The title compound was synthesized in analogy to example 1, from 5-(4-isopropyl-piperazine-1-carbonyl)-1H-indole-2-carboxylic acid hydrochloride (example 1, intermediate b), and 1-(piperidin-1-yl-sulfonyl)-piperazine to afford the desired product as a light-brown solid (87%). MS (ISP): 531.2 (M+H)$^+$.

Example 3

[1-Cyclopropylmethyl-5-(4-isopropyl-piperazine-1-carbonyl)-1H-indol-2-yl]-[4-(piperidine-1-sulfonyl)-piperazin-1-yl]-methanone A suspension of 0.15 g (0.28 mmol) [5-(4-isopropyl-piperazine-1-carbonyl)-1H-indol-2-yl]-[4-(piperidine-1-sulfonyl)-piperazin-1-yl]-methanone (example 2) and 14 mg (0.32 mmol; 55% dispersion in mineral oil) sodium hydride in 2 mL N,N-dimethyl-formamide was stirred 20 min. at 70° C. 34 μL (48 mg, 0.35 mmol) cyclopropylmethyl bromide were added and the solution was stirred another 45 min. at 70° C. After cooling to room temperature, the mixture was poured into 10% aqueous ammonium chloride solution and the phases were separated. The aqueous phase was extracted three times with ethyl acetate. The combined organic layers were washed three times with water, brine, dried over magnesium sulfate, filtered and evaporated. The crude product was purified by flash chromatography on silica gel with dichloromethane:methanol (9:1 v/v) as eluant to give 0.15 g (91%) of the desired compound as colorless foam. MS (ISP): 585.3 (M+H)$^+$.

Example 4

[5-(4-Isopropyl-piperazine-1-carbonyl)-1-(2,2,2-trifluoro-ethyl)-1H-indol-2-yl]-[4-(piperidine-1-sulfonyl)-piperazin-1-yl]-methanone The title compound was synthesized in analogy to example 3, from [5-(4-isopropyl-piperazine-1-carbonyl)-1H-indol-2-yl]-[4-(piperidine-1-sulfonyl)-piperazin-1-yl]-methanone (example 2) and 2,2,2-trifluoroethyl methanesulfonate, to afford the desired product as a colorless foam (86%). MS (ISP): 613.3 (M+H)$^+$.

Example 5

[1-(3-Chloro-phenyl)-5-(4-isopropyl-piperazine-1-carbonyl)-1H-indol-2-yl]-(4-methanesulfonyl-piperazin-1-yl)-methanone A suspension of 0.20 g (0.43 mmol) [5-(4-isopropyl-piperazine-1-carbonyl)-1H-indol-2-yl]-(4-methanesulfonyl-piperazin-1-yl)-methanone (example 1), 0.20 g (1.30 mmol) 3-chlorophenylboronic acid, 0.16 g (0.86 mmol) copper(II) acetate and 0.14 mL (0.14 g, 1.73 mmol) pyridine in 5 mL chloroform was stirred 4.5 days at room temperature. The volatile components were evaporated under reduced pressure and the residue was purified by flash chromatography on silica gel with a gradient of dichloromethane:methanol (100:0 to 75:25 v/v) as eluant to afford 105 mg (42%) of the desired compound as a light-brown foam. MS (ISP): 572.2 (M+H)$^+$.

Example 6

[5-(4-Isopropyl-piperazine-1-carbonyl)-1-(3-trifluoromethyl-phenyl)-1H-indol-2-yl]-(4-methanesulfonyl-piperazin-1-yl)-methanone The title compound was synthesized in analogy to example 5, from [5-(4-isopropylpiperazine-1-carbonyl)-1H-indol-2-yl]-(4-methanesulfonyl-piperazin-1-yl)-methanone (example 1) and 3-(trifluoromethyl)phenylboronic acid to afford the desired product as a light-brown foam (68%). MS (ISP): 606.0 (M+H)$^+$.

Example 7

[1-(2-Chloro-pyridin-4-yl)-5-(4-isopropyl-piperazine-1-carbonyl)-1H-indol-2-yl]-(4-methanesulfonyl-piperazin-1-yl)-methanone The title compound was synthesized in analogy to example 5, from [5-(4-isopropyl-piperazine-1-carbonyl)-1H-indol-2-yl]-(4-methanesulfonyl-piperazin-1-yl)-methanone (example 1) and 2-chloropyridine-4-boronic acid to afford the desired product as a light-brown solid (32%). MS (ISP): 573.3 (M+H)$^+$.

Example 8

[1-Cyclopropylmethyl-5-(4-isopropyl-piperazine-1-carbonyl)-1H-indol-2-yl]-(4-methanesulfonyl-piperazin-1-yl)-methanone The title compound was synthesized in analogy to example 3, from [5-(4-isopropyl-piperazine-1-carbonyl)-1H-indol-2-yl]-(4-methanesulfonyl-piperazin-1-yl)-methanone (example 1) and cyclopropylmethyl bromide to afford the desired product as a colorless foam (54%). MS (ISP): 516.2 (M+H)$^+$.

Example 9

[5-(4-Isopropyl-piperazine-1-carbonyl)-1-(2,2,2-trifluoro-ethyl)-1H-indol-2-yl]-(4-methanesulfonyl-piperazin-1-yl)-methanone The title compound was synthesized in analogy to example 3, from [5-(4-isopropyl-piperazine-1-carbonyl)-1H-indol-2-yl]-(4-methanesulfonyl-piperazin-1-yl)-methanone (example 1) and 2,2,2-trifluoroethyl-methanesulfonate to afford the desired product as a colorless foam (54%). MS (ISP): 544.3 (M+H)$^+$.

Example 10

[1-(3-Chloro-phenyl)-5-(4-isopropyl-piperazine-1-carbonyl)-1H-indol-2-yl]-[4-(piperidine-1-sulfonyl)-piperazin-1-yl]-methanone The title compound was synthesized in analogy to example 5, from [5-(4-isopropyl-piperazine-1-carbonyl)-1H-indol-2- yl]-[4-(piperidine-1-sulfonyl)-piperazin-1-yl]-methanone (example 2) and 3-chlorophenylboronic acid to afford the desired product as a colorless foam (54%). MS (ISP): 641.5 (M+H)⁺.

Example 11

[5-(4-Isopropyl-piperazine-1-carbonyl)-1-(3-trifluoromethyl-phenyl)-1H-indol-2-yl]-[4-(piperidine-1-sulfonyl)-piperazin-1-yl]-methanone The title compound was synthesized in analogy to example 5, from [5-(4-isopropyl-piperazine-1-carbonyl)-1H-indol-2-yl]-[4-(piperidine-1-sulfonyl)-piperazin-1-yl]-methanone (example 2) and 3-(trifluoromethyl)phenylboronic acid to afford the desired product as a colorless foam (67%). MS (ISP): 675.2 (M+H)⁺.

Example 12

[1-(2-Chloro-pyridin-4-yl)-5-(4-isopropyl-piperazine-1-carbonyl)-1H-indol-2-yl]-[4-(piperidine-1-sulfonyl)-piperazin-1-yl]-methanone The title compound was synthesized in analogy to example 5, from [5-(4-isopropyl-piperazine-1-carbonyl)-1H-indol-2-yl]-[4-(piperidine-1-sulfonyl)-piperazin-1-yl]-methanone (example 2) and 2-chloropyridine-4-boronic acid to afford the desired product as a colorless foam (31%). MS (ISP): 642.5 (M+H)⁺.

Example 13

(4-Benzenesulfonyl-piperazin-1-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid hydrochloride (example 1, intermediate b) and 1-benzenesulfonyl-piperazine to afford the desired product as a light-brown foam (92%). MS (ISP): 524.2 (M+H)⁺.

Example 14

{4-[5-(4-Isopropyl-piperazine-1-carbonyl)-1H-indole-2-carbonyl]-piperazin-1-yl}-piperidin-1-yl-methanone The title compound was synthesized in analogy to example 1, from 5-(4-isopropyl-piperazine-1-carbonyl)-1H-indole-2-carboxylic acid hydrochloride (example 1, intermediate b) and piperazin-1-yl-piperidin-1-yl-methanone to afford the desired product as a light-brown foam (95%). MS (ISP): 495.5 (M+H)⁺

Example 15

[5-(4-Isopropyl-piperazine-1-carbonyl)-1H-indol-2-yl]-[4-(propane-2-sulfonyl)-piperazin-1-yl]-methanone The title compound was synthesized in analogy to example 1, from 5-(4-isopropyl-piperazine-1-carbonyl)-1H-indole-2-carboxylic acid hydrochloride (example 1, intermediate b) and 1-(1-methylethylsulfonyl)piperazine (prepared in analogy to WO2003064413 using isopropylsulfonyl chloride and tert-butyl 1-piperazinecarboxylate) to afford the desired product as a light-brown solid (87%). MS (ISP): 490.3 (M+H)⁺.

Example 16

(4-Benzenesulfonyl-piperazin-1-yl)-[1-(3-chlorophenyl)-5-(4-isopropyl-piperazine-1-carbonyl)-1H-indol-2-yl]-methanone The title compound was synthesized in analogy to example 5, from (4-benzenesulfonyl-piperazin-1-yl)-[5-(4-isopropyl-piperazine-1-carbonyl)-1H-indol-2-yl]-methanone (example 13) and 3-chlorophenylboronic acid to afford the desired product as a light brown foam (47%). MS (ISP): 634.3 (M+H)⁺.

Example 17

(4-Benzenesulfonyl-piperazin-1-yl)-[1-(2-chloropyridin-4-yl)-5-(4-isopropyl-piperazine-1-carbonyl)-1H-indol-2-yl]-methanone The title compound was synthesized in analogy to example 5, from (4-benzenesulfonyl-piperazin-1-yl)-[5-(4-isopropyl-piperazine-1-carbonyl)-1H-indol-2-yl]-methanone (example 13) and 2-chloropyridine-4-boronic acid to afford the desired product as a light brown solid (44%). MS (ISP): 635.3 (M+H)⁺.

Example 18

[1-(3-Chloro-phenyl)-5-(4-isopropyl-piperazine-1-carbonyl)-1H-indol-2-yl]-[4-(piperidine-1-carbonyl)-piperazin-1-yl]-methanone The title compound was synthesized in analogy to example 5, from {4-[5-(4-isopropyl-piperazine-1-carbonyl)-1H-indole-2-carbonyl]-piperazin-1-yl}-piperidin-1-yl-methanone (example 14) and 3-chlorophenylboronic acid to afford the desired product as a light-brown foam (49%). MS (ISP): 605.2 (M+H)⁺.

Example 19

[1-(2-Chloro-pyridin-4-yl)-5-(4-isopropyl-piperazine-1-carbonyl)-1H-indol-2-yl]-[4-(piperidine-1-carbonyl)-piperazin-1-yl]-methanone The title compound was synthesized in analogy to example 5, after stirring for 3.5 days at 35° C., from {4-[5-(4-isopropyl-piperazine-1-carbonyl)-1H-indole-2-carbonyl]-piperazin-1-yl}-piperidin-1-yl-methanone (example 14) and 2-chloropyridine-4-boronic acid to afford the desired product as a light-brown foam (62%). MS (ISP): 606.1 (M+H)⁺.

Example 20

[1-(3-Chloro-phenyl)-5-(4-isopropyl-piperazine-1-carbonyl)-1H-indol-2-yl]-[4-(propane-2-sulfonyl)-piperazin-1-yl]-methanone The title compound was synthesized in analogy to example 5, after stirring for 3.5 days at 35° C., from [5-(4-isopropyl-piperazine-1-carbonyl)-1H-indol-2-yl]-[4-(propane-2-sulfonyl)-piperazin-1-yl]-methanone (example 15) and 3-chlorophenylboronic acid to afford the desired product as a colorless foam (65%). MS (ISP): 600.4 (M+H)$^+$.

Example 21

[1-(2-Chloro-pyridin-4-yl)-5-(4-isopropyl-piperazine-1-carbonyl)-1H-indol-2-yl]-[4-(propane-2-sulfonyl)-piperazin-1-yl]-methanone The title compound was synthesized in analogy to example 5, after stirring for 3.5 days at 35° C., from [5-(4-isopropyl-piperazine-1-carbonyl)-1H-indol-2-yl]-[4-(propane-2-sulfonyl)-piperazin-1-yl]-methanone (example 15) and 2-chloropyridine-4-boronic acid to afford the desired product as a light-brown foam (41%). MS (ISP): 601.4 (M+H)$^+$.

Example 22

(4-Benzenesulfonyl-piperazin-1-yl)-[1-isopropyl-5-(4-isopropyl-piperazine-1-carbonyl)-1H-indol-2-yl]-methanone A suspension of 0.20 g (0.38 mmol) (4-benzenesulfonyl-piperazin-1-yl)-[5-(4-isopropyl-piperazine-1-carbonyl)-1H-indol-2-yl]-methanone (example 13), 0.25 g (0.77 mmol) caesium carbonate and isopropyl methanesulfonate in 4 mL acetonitrile was heated 16 h under reflux. After cooling to room temperature, the mixture was poured into saturated aqueous sodium bicarbonate solution and the phases were separated. The aqueous phase was extracted three times with ethyl acetate. The combined organic layers were washed with brine, dried over magnesium sulfate, filtered and evaporated. The crude product was purified by flash chromatography on silica gel with dichloromethane:methanol (19:1 v/v) as eluant to afford 0.85 g (39%) of the desired compound as a light brown foam. MS (ISP): 566.4 (M+H)$^+$.

Example 23

[1-Isopropyl-5-(4-isopropyl-piperazine-1-carbonyl)-1H-indol-2-yl]-[4-(piperidine-1-carbonyl)-piperazin-1-yl]-methanone The title compound was synthesized in analogy to example 22, from {4-[5-(4-isopropyl-piperazine-1-carbonyl)-1H-indole-2-carbonyl]-piperazin-1-yl}-piperidin-1-yl-methanone (example 14) to afford the desired product as a colorless foam (34%). MS (ISP): 537.5 (M+H)$^+$.

Example 24

[1-Isopropyl-5-(4-isopropyl-piperazine-1-carbonyl)-1H-indol-2-yl]-[4-(propane-2-sulfonyl)-piperazin-1-yl]-methanone The title compound was synthesized in analogy to example 22, from [5-(4-isopropyl-piperazine-1-carbonyl)-1H-indol-2-yl]-[4-(propane-2-sulfonyl)-piperazin-1-yl]-methanone (example 15) to afford the desired product as a colorless foam (56%). MS (ISP): 532.4 (M+H)$^+$.

Example 25

(4-Cyclopropanecarbonyl-piperazin-1-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid hydrochloride (example 1, intermediate b), and cyclopropylcarboxylic acid 1-piperazineamide hydrochloride to afford the desired product as a light-brown foam (89%). MS (ISP): 452.2 (M+H)$^+$.

Example 26

(4-Cyclopropanecarbonyl-piperazin-1-yl)-[1-isopropyl-5-(4-isopropyl-piperazine-1-carbonyl)-1H-indol-2-yl]-methanone The title compound was synthesized in analogy to example 22, from (4-cyclopropanecarbonyl-piperazin-1-yl)-[5-(4-isopropyl-piperazine-1-carbonyl)-1H-indol-2-yl]-methanone (example 25) to afford the desired product as a colorless foam (57%). MS (ISP): 494.3 (M+H)$^+$.

Example 27

[1-(2-Chloro-pyridin-4-yl)-5-(4-isopropyl-piperazine-1-carbonyl)-1H-indol-2-yl]-(4-cyclopropanecarbonyl-piperazin-1-yl)-methanone The title compound was synthesized in analogy to example 5, after stirring for 6.5 days at 35° C., from (4-cyclopropanecarbonyl-piperazin-1-yl)-[5-(4-isopropyl-piperazine-1-carbonyl)-1H-indol-2-yl]-methanone (example 25) and 2-chloropyridine-4-boronic acid to afford the desired product as a colorless foam (43%). MS (ISP): 563.5 (M+H)$^+$.

Example 28

[1-(6-Chloro-pyridin-3-yl)-5-(4-isopropyl-piperazine-1-carbonyl)-1H-indol-2-yl]-(4-cyclopropanecarbonyl-piperazin-1-yl)-methanone The title compound was synthesized in analogy to example 5, after stirring for 6.5 days at 35° C., from (4-cyclopropanecarbonyl-piperazin-1-yl)-[5-(4-isopropyl-piperazine-1-carbonyl)-1H-indol-2-yl]-methanone (example 25) and 2-chloropyridine-5-boronic acid to afford the desired product as a colorless foam (33%). MS (ISP): 563.5 (M+H)$^+$.

Example 29

[1-(3-Chloro-phenyl)-5-(4-isopropyl-piperazine-1-carbonyl)-1H-indol-2-yl]-(4-cyclopropanecarbonyl-piperazin-1-yl)-methanone The title compound was synthesized in analogy to example 5, after stirring for 6.5 days at 35° C., from (4-cyclopropanecarbonyl-piperazin-1-yl)-[5-(4-isopropyl-piperazine-1-carbonyl)-1H-indol-2-yl]-methanone (example 25) and 3-chlorophenylboronic acid to afford the desired product as a colorless gum (53%). MS (ISP): 562.5 (M+H)$^+$.

Example 30

(4-Cyclopropanecarbonyl-piperazin-1-yl)-[5-(4-isopropyl-piperazine-1-carbonyl)-1-(3-trifluoromethyl-phenyl)-1H-indol-2-yl]-methanone The title compound was synthesized in analogy to example 5, after stirring for 6.5 days at 35° C., from (4-cyclopropanecarbonyl-piperazin-1-yl)-[5-(4-isopropyl-piperazine-1-carbonyl)-1H-indol-2-yl]-methanone (example 25) and 3-(trifluoromethyl)-phenylboronic acid to afford the desired product as a colorless gum (79%). MS (ISP): 596.3 (M+H)$^+$.

Example 31

1-{4-[5-(4-Isopropyl-piperazine-1-carbonyl)-1H-indole-2-carbonyl]-piperazin-1-yl}-2-methyl-propan-1-one The title compound was synthesized in analogy to example 1, from 5-(4-isopropyl-piperazine-1-carbonyl)-1H-indole-2-carboxylic acid hydrochloride (example 1, intermediate b) and 1-(2-methylpropanoyl)-piperazine to afford the desired product as light-brown foam (91%). MS (ISP): 454.3 (M+H)$^+$.

Example 32

4-[5-(4-Isopropyl-piperazine-1-carbonyl)-1H-indole-2-carbonyl]-piperazine-1-carboxylic acid dimethylamide The title compound was synthesized in analogy to example 1, from 5-(4-isopropyl-piperazine-1-carbonyl)-1H-indole-2-carboxylic acid hydrochloride (example 1, intermediate b) and piperazine-1-carboxylic acid dimethylamide to afford the desired product as light-brown foam (59%). MS (ISP): 455.4 (M+H)$^+$.

Example 33

(4-Cyclopropanesulfonyl-piperazin-1-yl)-[5-(4-isopropyl-piperazine-1-carbonyl)-1H-indol-2-yl]-methanone The title compound was synthesized in analogy to example 1, from 5-(4-isopropyl-piperazine-1-carbonyl)-1H-indole-2-carboxylic acid hydrochloride (example 1, intermediate b) and cyclopropylsulfonyl-piperazine to afford the desired product as light brown foam (93%). MS (ISP): 488.1 (M+H)$^+$.

Example 34

1-{4-[1-(2-Chloro-pyridin-4-yl)-5-(4-isopropyl-piperazine-1-carbonyl)-1H-indole-2-carbonyl]-piperazin-1-yl}-2-methyl-propan-1-one The title compound was synthesized in analogy to example 5, after stirring for 6.5 days at 35° C., from 1-{4-[5-(4-isopropyl-piperazine-1-carbonyl)-1H-indole-2-carbonyl]-piperazin-1-yl}-2-methyl-propan-1-one (example 31) and 2-chloropyridine-4-boronic acid to afford the desired product as light-brown foam (43%). MS (ISP): 565.4 (M+H)$^+$.

Example 35

1-{4-[1-(6-Chloro-pyridin-3-yl)-5-(4-isopropyl-piperazine-1-carbonyl)-1H-indole-2-carbonyl]-piperazin-1-yl}-2-methyl-propan-1-one The title compound was synthesized in analogy to example 5, after stirring for 6.5 days at 35° C., from 1-{4-[5-(4-isopropyl-piperazine-1-carbonyl)-1H-indole-2-carbonyl]-piperazin-1-yl}-2-methyl-propan-1-one (example 31) and 2-chloropyridine-5-boronic acid to afford the desired product as a light-brown foam (43%). MS (ISP): 565.4 (M+H)$^+$.

Example 36

1-{4-[1-(3-Chloro-phenyl)-5-(4-isopropyl-piperazine-1-carbonyl)-1H-indole-2-carbonyl]-piperazin-1-yl}-2-methyl-propan-1-one The title compound was synthesized in analogy to example 5, from 1-{4-[5-(4-isopropyl-piperazine-1-carbonyl)-1H-indole-2-carbonyl]-piperazin-1-yl}-2-methyl-propan-1-one (example 31) and 3-chlorophenylboronic acid to afford the desired product as a light-brown foam (47%). MS (ISP): 564.5 (M+H)$^+$.

Example 37

[1-(2-Chloro-pyridin-4-yl)-5-(4-isopropyl-piperazine-1-carbonyl)-1H-indol-2-yl]-(4-cyclopropanesulfonyl-piperazin-1-yl)-methanone The title compound was synthesized in analogy to example 5, from (4-cyclopropanesulfonyl-piperazin-1-yl)-[5-(4-isopropyl-piperazine-1-carbonyl)-1H-indol-2-yl]-methanone (example 33) and 2-chloropyridine-4-boronic acid to afford the desired product as light-brown foam (61%). MS (ISP): 599.4 (M+H)$^+$.

Example 38

[1-(6-Chloro-pyridin-3-yl)-5-(4-isopropyl-piperazine-1-carbonyl)-1H-indol-2-yl]-(4-cyclopropanesulfonyl-piperazin-1-yl)-methanone The title compound was synthesized in analogy to example 5, from (4-cyclopropanesulfonyl-piperazin-1-yl)-[5-(4-isopropyl-piperazine-1-carbonyl)-1H-indol-2-yl]-methanone (example 33) and 2-chloropyridine-5-boronic acid to afford the desired product as light brown foam (44%). MS (ISP): 599.4 (M+H)$^+$.

Example 39

[1-(3-Chloro-phenyl)-5-(4-isopropyl-piperazine-1-carbonyl)-1H-indol-2-yl]-(4-cyclopropanesulfonyl-piperazin-1-yl)-methanone The title compound was synthesized in analogy to example 5, from (4-cyclopropanesulfonyl-piperazin-1-yl)-[5-(4-isopropyl-piperazine-1-carbonyl)-1H-indol-2-yl]-methanone (example 33) and 3-chlorophenylboronic acid to afford the desired product as a light brown foam (41%). MS (ISP): 598.3 (M+H)$^+$.

Example 40

4-[1-(2-Chloro-pyridin-4-yl)-5-(4-isopropyl-piperazine-1-carbonyl)-1H-indole-2-carbonyl]-piperazine-1-carboxylic The title compound was synthesized in analogy to example 5, from 4-[5-(4-isopropyl-piperazine-1-carbonyl)-1H-indole-2-carbonyl]-piperazine-1-carboxylic acid dimethylamide (example 32) and 2-chloropyridine-4-boronic acid to afford the desired product as a light brown foam (40%). MS (ISP): 566.4 (M+H)$^+$.

Example 41

1-{4-[1-Isopropyl-5-(4-isopropyl-piperazine-1-carbonyl)-1H-indole-2-carbonyl]-piperazin-1-yl}-2-methyl-propan-1-one The title compound was synthesized in analogy to example 22, from 1-{4-[5-(4-isopropyl-piperazine-1-carbonyl)-1H-indole-2-carbonyl]-piperazin-1-yl}-2-methyl-propan-1-one (example 31) to afford the desired product as a colorless foam (69%). MS (ISP): 496.2 (M+H)$^+$.

Example 42

(4-Cyclopropanesulfonyl-piperazin-1-yl)-[1-isopropyl-5-(4-isopropyl-piperazine-1-carbonyl)-1H-indol-2-yl]-methanone The title compound was synthesized in analogy to example 22, from (4-cyclopropanesulfonyl-piperazin-1-yl)-[5-(4-isopropyl-piperazine-1-carbonyl)-1H-indol-2-yl]-methanone (example 33) to afford the desired product as a colorless foam (46%). MS (ISP): 530.2 (M+H)$^+$.

Example 43

4-[5-(4-Isopropyl-piperazine-1-carbonyl)-1H-indole-2-carbonyl]-piperazine-1-carboxylic acid ethyl ester The title compound was synthesized in analogy to example 1, from 5-(4-isopropyl-piperazine-1-carbonyl)-1H-indole-2-carboxylic acid hydrochloride (example 1, intermediate b) and 1-ethoxycarbonylpiperazine to afford the desired product as a light-brown solid (72%). MS (ISP): 456.3 (M+H)$^+$.

Example 44

4-[1-Isopropyl-5-(4-isopropyl-piperazine-1-carbonyl)-1H-indole-2-carbonyl]-piperazine-1-carboxylic acid dimethylamide The title compound was synthesized in analogy to example 22, from 4-[5-(4-isopropyl-piperazine-1-carbonyl)-1H-indole-2-carbonyl]-piperazine-1-carboxylic acid dimethylamide (example 32) to afford the desired product as a colorless foam (68%). MS (ISP): 497.2 (M+H)$^+$.

Example 45

4-[1-Isopropyl-5-(4-isopropyl-piperazine-1-carbonyl)-1H-indole-2-carbonyl]-piperazine-1-carboxylic acid ethyl ester The title compound was synthesized in analogy to example 22, from 4-[5-(4-isopropyl-piperazine-1-carbonyl)-1H-indole-2-carbonyl]-piperazine-1-carboxylic acid ethyl ester (example 43) to afford the desired product as a colorless foam (53%). MS (ISP): 498.2 (M+H)$^+$.

Example 46

4-[1-(2-Chloro-pyridin-4-yl)-5-(4-isopropyl-piperazine-1-carbonyl)-1H-indole-2-carbonyl]-piperazine-1-carboxylic acid ethyl ester The title compound was synthesized in analogy to example 5, from 4-[5-(4-isopropyl-piperazine-1-carbonyl)-1H-indole-2-carbonyl]-piperazine-1-carboxylic acid ethyl ester (example 43) and 2-chloropyridine-4-boronic acid to give the desired product as a light-yellow foam (60%). MS (ISP): 567.4 (M+H)$^+$.

Example 47

4-[1-Isopropyl-5-(4-isopropyl-[1,4]diazepane-1-carbonyl)-1H-indole-2-carbonyl]-piperazine-1-carboxylic acid ethyl ester To a solution of 4-[2-(4-ethoxycarbonyl-piperazine-1-carbonyl)-1-isopropyl-1H-indole-5-carbonyl]-[1,4]diazepane-1-carboxylic acid tert-butyl ester (195 mg, 0.1 mmol) in ethyl acetate (10 ml) was added 5M hydrogen chloride in ethyl acetate (5 eq, 0.34 ml) dropwise. The mixture was stirred two days at room temperature. The mixture was evaporated to dryness under reduced pressure to afford the HCl salt of the deprotected amine as an off-white solid. The solid was suspended in 1,2-dichloromethane (10 ml) and triethylamine (0.1 ml) added dropwise, followed after 10 min by acetone (10 eq., 0.25 ml) and sodium triacetoxyborohydride (3 eq., 218 mg). The mixture was stirred for two days at room temperature. Sodium bicarbonate was added and the mixture stirred vigorously 1 h. The crude mixture was purified by column chromatography on silica gel (9:1 CHCl$_3$/MeOH eluant) to afford the product as a white powder (117 mg, 66%). MS (m/z): 512.4 (M+H)$^+$.

Intermediates a) 4-[2-(4-Ethoxycarbonyl-piperazine-1-carbonyl)-1-isopropyl-1H-indole-5-carbonyl]-[1,4]diazepane-1-carboxylic acid tert-butyl ester To a mixture of 5-(4-tert-butoxycarbonyl-[1,4]diazepane-1-carbonyl)-1-isopropyl-1H-indole-2-carboxylic acid (144 mg) and 4-ethoxy carbonyl piperazine (1 eq., 53 mg) in acetonitrile (5 ml) was added N-hydroxybenzotriazole (0.2 eq., 9 mg). The mixture was stirred 5 min before the addition of N-(3-dimethylaminopropyl)-N'-ethyl-carbodiimide hydrochloride (1.1 eq., 77 mg). The mixture was stirred two days at room temperature. The mixture was evaporated under reduced pressure and the residue purified by column chromatography on silica gel (19:1 EtOAc/MeOH) to afford the product as an off-white powder (195 mg, 89%). MS (m/z): 570.3 (M+H)$^+$.

b) 5-(4-tert-Butoxycarbonyl-[1,4]diazepane-1-carbonyl)-1-isopropyl-1H-indole-2-carboxylic acid To a solution of 5-(4-tert-butoxycarbonyl-[1,4]diazepane-1-carbonyl)-1-isopropyl-1H-indole-2-carboxylic acid ethyl ester (1.60 g, 3.5 mmol) in tetrahydrofuran (10 ml), methanol (10 ml) and water (2 ml) was added lithium hydroxide monohydrate (2 eq., 168 mg). The mixture was stirred two days at room temperature. The solvent was removed under vacuum and the residue was quenched with 1M aq. dihydrogen potassium phosphate solution to pH 5. The aqueous phase was extracted with ethyl acetate (2×) and the combined organic phases washed with brine, dried over MgSO$_4$ and filtered. The crude product was purified by column chromatography on silica gel (3:1 heptane/ethyl acetate eluant) to afford the product as an off-white powder (644 mg, 42%). MS (m/z): 430.3 (M+H)$^+$.

c) 5-(4-tert-Butoxycarbonyl-[1,4]diazepane-1-carbonyl)-1-isopropyl-1H-indole-2-carboxylic acid ethyl ester To a solution of 5-(4-tert-butoxycarbonyl-[1,4]diazepane-1-carbonyl)-1H-indole-2-carboxylic acid ethyl ester (1.55 g, 3.5 mmol) in acetonitrile (25 ml) under an argon atmosphere were added caesium carbonate (2 eq., 2.44 g) and isopropylmethanesulfonate (2 eq., 1.03 g). The mixture was heated at 95° C. (oil-bath temperature) overnight. The mixture was cooled to room temperature and evaporated under reduced pressure. The crude product was purified by column chromatography on silica gel (3:1 heptane/ethyl acetate eluant) to afford the product as a light-brown oil (1.6 g, 93%). MS (m/z): 458.3 (M+H)$^+$.

d) 5-(4-tert-Butoxycarbonyl-[1,4]diazepane-1-carbonyl)-1H-indole-2-carboxylic acid ethyl ester To a solution of 1H-indole-2,5-dicarboxylic acid 2-ethyl ester (3.08 g, 13 mmol) and tert-butyl 1-homopiperazinecarboxylate (1 eq., 2.657 g) in DMF (50 ml) was added N-hydroxybenzotriazole (0.2 eq., 360 mg). After a five minutes, N-(3-dimethylaminopropyl)-N'-ethyl-carbodiimide hydrochloride (1.2 eq., 3.05 g) was added and the mixture stirred at room temperature overnight. The solvent was removed under reduced pressure and the crude product was purified by column chromatography on silica gel (3:1 heptane/ethyl acetate eluant) to afford the product as a light-brown solid (5.21 g, 94%). MS (m/z): 416.4 (M+H)$^+$.

Example 48

4-[1-Isopropyl-5-(4-isopropyl-[1,4]diazepane-1-carbonyl)-1H-indole-2-carbonyl]-piperazine-1-carboxylic acid dimethylamide The title compound was synthesized in analogy to example 47, from 4-[2-(4-dimethylcarbamoyl-piperazine-1-carbonyl)-1-isopropyl-1H-indole-5-carbonyl]-[1,4]diazepane-1-carboxylic acid tert-butyl ester. Light-yellow solid. MS (m/z): 511.8 (M+H)$^+$.

Intermediates a) 4-[2-(4-Dimethylcarbamoyl-piperazine-1-carbonyl)-1-isopropyl-1H-indole-5-carbonyl]-[1,4]diazepane-1-carboxylic acid tert-butyl ester The title compound was synthesized in analogy to example 47a), from 5-(4-tert-butoxycarbonyl-[1,4]diazepane-1-carbonyl)-1-isopropyl-1H-indole-2-carboxylic acid and piperazine carboxylic acid dimethylamide. Off-white solid. MS (m/z): 569.4 (M+H)$^+$.

Example 49

(4-Methanesulfonyl-piperazin-1-yl)-{5-[4-(tetrahydro-pyran-4-yl)-[1,4]diazepane-1-carbonyl]-1H-indol-2-yl}-methanone The title compound was synthesized in analogy to example 47, from 4-[2-(4-methanesulfonyl-piperazine-1-carbonyl)-1H-indole-5-carbonyl]-[1,4]diazepane-1-carboxylic acid tert-butyl ester and tetrahydro-4H-pyran-4-one. Yellow gum. MS (m/z): 518.3 (M+H)$^+$.

Intermediates a) 4-[2-(4-Methanesulfonyl-piperazine-1-carbonyl)-1H-indole-5-carbonyl]-[1,4]diazepane-1-carboxylic acid tert-butyl ester The title compound was synthesized in analogy to example 47a), from 5-(4-tert-butoxycarbonyl-[1,4]diazepane-1-carbonyl)-1H-indole-2-carboxylic acid and 1-methanesulfonyl-piperazine hydrochloride. Off-white powder. MS (m/z): 534.4 (M+H)$^+$.

b) 5-(4-tert-Butoxycarbonyl-[1,4]diazepane-1-carbonyl)-1H-indole-2-carboxylic acid The title compound was synthesized in analogy to example 47b), from 5-(4-tert-butoxycarbonyl-[1,4]diazepane-1-carbonyl)-1H-indole-2-carboxylic acid ethyl ester. Light-brown gum. MS (m/z): 386.4 (M−H)$^-$.

Example 50

4-[5-(4-Cyclobutyl-[1,4]diazepane-1-carbonyl)-1H-indole-2-carbonyl]-piperazine-1-carboxylic acid ethyl ester The title compound was synthesized in analogy to example 47, from 4-[2-(4-ethoxycarbonyl-piperazine-1-carbonyl)-1H-indole-5-carbonyl]-[1,4]diazepane-1-carboxylic acid tert-butyl ester and cyclobutanone. Light-yellow solid. MS (m/z): 482.4 (M+H)$^+$.

Intermediate

4-[2-(4-Ethoxycarbonyl-piperazine-1-carbonyl)-1H-indole-5-carbonyl]-[1,4]diazepane-1-carboxylic acid tert-butyl ester The title compound was synthesized in analogy to example 47a), from 5-(4-tert-butoxycarbonyl-[1,4]diazepane-1-carbonyl)-1H-indole-2-carboxylic acid and 4-ethoxycarbonylpiperazine. Off-white solid. MS (m/z): 505.2 (M+H)$^+$.

Example 51

[5-(4-Isopropyl-[1,4]diazepane-1-carbonyl)-1H-indol-2-yl]-(4-methanesulfonyl-piperazin-1-yl)-methanone The title compound was synthesized in analogy to example 47a), from 4-[2-(4-methanesulfonyl-piperazine-1-carbonyl)-1H-indole-5-carbonyl]-[1,4]diazepane-1-carboxylic acid tert-butyl ester. Light-yellow solid. MS (m/z): 476.0 (M+H)$^+$.

Example 52

4-[5-(4-Isopropyl-[1,4]diazepane-1-carbonyl)-1H-indole-2-carbonyl]-piperazine-1-carboxylic acid ethyl ester The title compound was synthesized in analogy to example 47, from 4-[2-(4-ethoxycarbonyl-piperazine-1-carbonyl)-1H-indole-5-carbonyl]-[1,4]diazepane-1-carboxylic acid tert-butyl ester. Off-white solid. MS (m/z): 470.5 (M+H)$^+$.

Example 53

4-[5-(4-Isopropyl-[1,4]diazepane-1-carbonyl)-1H-indole-2-carbonyl]-piperazine-1-carboxylic acid dimethylamide The title compound was synthesized in analogy to example 47, from 4-[2-(4-dimethylcarbamoyl-piperazine-1-carbonyl)-1H-indole-5-carbonyl]-[1,4]diazepane-1-carboxylic acid tert-butyl ester. Light-yellow solid. MS (m/z): 469.3 $(M+H)^+$.

Intermediate a) 4-[2-(4-Dimethylcarbamoyl-piperazine-1-carbonyl)-1H-indole-5-carbonyl]-[1,4]diazepane-1-carboxylic acid tert-butyl ester The title compound was synthesized in analogy to example 47a), from 5-(4-tert-butoxycarbonyl-[1,4]diazepane-1-carbonyl)-1H-indole-2-carboxylic acid and piperazine-1-carboxylic acid dimethyl amide. White solid. MS (m/z): 527.3 $(M+H)^+$.

Example 54

[1-Isopropyl-5-(4-isopropyl-[1,4]diazepane-1-carbonyl)-1H-indol-2-yl]-(4-methanesulfonyl-piperazin-1-yl)-methanone The title compound was synthesized in analogy to example 47, from 4-[1-isopropyl-2-(4-methanesulfonyl-piperazine-1-carbonyl)-1H-indole-5-carbonyl]-[1,4]diazepane-1-carboxylic acid tert-butyl ester. Yellow solid. MS (m/z): 518.3 $(M+H)^+$.

Intermediate a) 4-[1-Isopropyl-2-(4-methanesulfonyl-piperazine-1-carbonyl)-1H-indole-5-carbonyl]-[1,4]diazepane-1-carboxylic acid tert-butyl ester The title compound was synthesized in analogy to example 47a), from 5-(4-tert-butoxycarbonyl-[1,4]diazepane-1-carbonyl)-1-isopropyl-1H-indole-2-carboxylic acid and 1-methanesulfonyl-piperazine hydrochloride. White solid. MS (m/z): 576.4 $(M+H)^+$.

Example A

Film coated tablets containing the following ingredients can be manufactured in a conventional manner:

| Ingredients | Per tablet | |
|---|---|---|
| Kernel: | | |
| Compound of formula (I) | 10.0 mg | 200.0 mg |
| Microcrystalline cellulose | 23.5 mg | 43.5 mg |
| Lactose hydrous | 60.0 mg | 70.0 mg |
| Povidone K30 | 12.5 mg | 15.0 mg |
| Sodium starch glycolate | 12.5 mg | 17.0 mg |
| Magnesium stearate | 1.5 mg | 4.5 mg |
| (Kernel Weight) | 120.0 mg | 350.0 mg |
| Film Coat: | | |
| Hydroxypropyl methyl cellulose | 3.5 mg | 7.0 mg |
| Polyethylene glycol 6000 | 0.8 mg | 1.6 mg |
| Talc | 1.3 mg | 2.6 mg |
| Iron oxide (yellow) | 0.8 mg | 1.6 mg |
| Titanium dioxide | 0.8 mg | 1.6 mg |

The active ingredient is sieved and mixed with microcrystalline cellulose and the mixture is granulated with a solution of polyvinylpyrrolidone in water. The granulate is mixed with sodium starch glycolate and magnesiumstearate and compressed to yield kernels of 120 or 350 mg respectively. The kernels are lacquered with an aqueous solution/suspension of the above mentioned film coat.

Example B

Capsules containing the following ingredients can be manufactured in a conventional manner:

| Ingredients | Per capsule |
|---|---|
| Compound of formula (I) | 25.0 mg |
| Lactose | 150.0 mg |
| Maize starch | 20.0 mg |
| Talc | 5.0 mg |

The components are sieved and mixed and filled into capsules of size 2.

Example C

Injection solutions can have the following composition:

| | |
|---|---|
| Compound of formula (I) | 3.0 mg |
| Gelatine | 150.0 mg |
| Phenol | 4.7 mg |
| Sodium carbonate | to obtain a final pH of 7 |
| Water for injection solutions | ad 1.0 ml |

Example D

Soft gelatin capsules containing the following ingredients can be manufactured in a conventional manner:

| | |
|---|---|
| Capsule contents | |
| Compound of formula (I) | 5.0 mg |
| Yellow wax | 8.0 mg |
| Hydrogenated Soya bean oil | 8.0 mg |
| Partially hydrogenated plant oils | 34.0 mg |
| Soya bean oil | 110.0 mg |
| Weight of capsule contents | 165.0 mg |
| Gelatin capsule | |
| Gelatin | 75.0 mg |
| Glycerol 85% | 32.0 mg |
| Karion 83 | 8.0 mg (dry matter) |

-continued

| | |
|---|---|
| Titanium dioxide | 0.4 mg |
| Iron oxide yellow | 1.1 mg |

The active ingredient is dissolved in a warm melting of the other ingredients and the mixture is filled into soft gelatin capsules of appropriate size. The filled soft gelatin capsules are treated according to the usual procedures.

Example E

Sachets containing the following ingredients can be manufactured in a conventional manner:

| | |
|---|---|
| Compound of formula (I) | 50.0 mg |
| Lactose, fine powder | 1015.0 mg |
| Microcrystalline cellulose (AVICEL PH 102) | 1400.0 mg |
| Sodium carboxymethyl cellulose | 14.0 mg |
| Polyvinylpyrrolidone K 30 | 10.0 mg |
| Magnesium stearate | 10.0 mg |
| Flavoring additives | 1.0 mg |

The active ingredient is mixed with lactose, microcrystalline cellulose and sodium carboxymethyl cellulose and granulated with a mixture of polyvinylpyrrolidone in water. The granulate is mixed with magnesium stearate and the flavoring additives and filled into sachets.

Unless stated to the contrary, all compounds in the examples were prepared and characterized as described. All ranges recited herein encompass all combinations and subcombinations included within that range limit. All patents and publications cited herein are hereby incorporated by reference in their entirety.

The invention claimed is:
1. A compound of formula I:

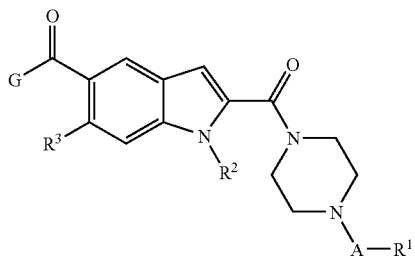

I or a pharmaceutically acceptable salt thereof, wherein:
A is C(O) or S(O)$_2$;
R$^1$ is selected from the group consisting of:
(1) lower alkyl,
(2) lower alkoxy,
(3) cycloalkyl,
(4) lower cycloalkylalkyl,
(5) lower halogenalkyl,
(6) phenyl unsubstituted or substituted with one to three substituents independently selected from the group consisting of lower alkyl, lower alkoxy, halogen, lower halogenalkyl and cyano, and
(7) —NR$^4$R$^5$, wherein R$^4$ and R$^5$ independently from each other are selected from the group consisting of lower alkyl, cycloalkyl, lower cycloalkylalkyl, lower halogenalkyl and lower phenylalkyl, or alternatively, R$^4$ and R$^5$ together with the nitrogen atom to which they are attached form a 5- or 6-membered heterocyclic ring optionally containing a further heteroatom of nitrogen, oxygen or sulfur;

R$^2$ is selected from the group consisting of:
(1) hydrogen,
(2) lower alkyl,
(3) cycloalkyl,
(4) lower cycloalkylalkyl,
(5) lower hydroxyalkyl,
(6) lower alkoxyalkyl,
(7) lower halogenalkyl,
(8) lower cyanoalkyl,
(9) lower alkylsulfonyl,
(10) lower alkanoyl,
(11) phenylsulfonyl wherein the phenyl ring may be unsubstituted or substituted with one to three substituents independently selected from the group consisting of lower alkyl, halogen, lower alkoxy, lower halogenalkoxy and lower hydroxyalkyl,
(12) phenyl unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino,
(13) benzodioxolyl,
(14) lower phenylalkyl, wherein the phenyl ring may be unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
(15) heteroaryl unsubstituted or substituted with one or two substituents independently selected from the group consisting of lower alkyl, lower alkoxy, cyano, morpholinyl and halogen;

R$^3$ is hydrogen, halogen or methyl;
G is either G1 or G2:

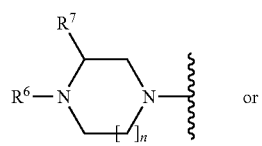

G1

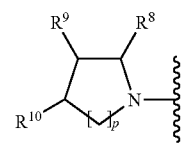

G2 wherein:
R$^6$ is lower alkyl, cycloalkyl, lower cycloalkylalkyl or a heterocyclic ring containing oxygen, and R$^7$ is hydrogen; or alternatively R$^6$ and R$^7$ together are —(CH$_2$)$_m$—, wherein m is 3 or 4, and are bonded to each other to form a ring together with the carbon or nitrogen atom to which they are attached;
n is 1 or 2;
p is 1 or 2;

$R^8$ is hydrogen;

$R^9$ and $R^{10}$ independently from each other are hydrogen or $-NR^{11}R^{12}$; and $R^{11}$ and $R^{12}$ independently from each other are lower alkyl or together with the nitrogen atom to which they are attached form a 5- or 6-membered saturated heterocyclic ring optionally containing a further heteroatom of nitrogen, oxygen or sulfur.

2. A compound of claim 1, wherein A is $S(O)_2$.

3. A compound of claim 1, wherein A is C(O).

4. A compound of claim 1, wherein $R^1$ is selected from the group consisting of:
   (1) lower alkyl,
   (2) lower alkoxy,
   (3) cycloalkyl,
   (4) phenyl unsubstituted or substituted with one to three substituents independently selected from the group consisting of lower alkyl, lower alkoxy, halogen, lower halogenalkyl and cyano, and
   (5) $-NR^4R^5$, wherein $R^4$ and $R^5$ independently from each other are selected from the group consisting of lower alkyl, cycloalkyl, lower cycloalkylalkyl, lower halogenalkyl and lower phenylalkyl, or alternatively, $R^4$ and $R^5$ together with the nitrogen atom to which they are attached form a 5- or 6-membered heterocyclic ring optionally containing a further heteroatom of nitrogen, oxygen or sulfur.

5. A compound of claim 1, wherein $R^1$ is lower alkyl, cycloalkyl, or phenyl.

6. A compound of claim 1, wherein $R^1$ is lower alkyl or cycloalkyl.

7. A compound of claim 1, wherein $R^1$ is $-NR^4R^5$, wherein $R^4$ and $R^5$ independently from each other are lower alkyl or wherein $R^4$ and $R^5$ together with the nitrogen atom they are attached to form a piperidine ring.

8. A compound of claim 1, wherein $R^1$ is lower alkoxy.

9. A compound of claim 1, wherein $R^2$ is selected from the group consisting of:
   (1) hydrogen,
   (2) lower alkyl,
   (3) cycloalkyl,
   (4) lower cycloalkylalkyl,
   (5) lower halogenalkyl,
   (6) phenyl unsubstituted or substituted with one to three substituents independently selected from the group consisting of lower alkyl, halogen, cyano, morpholinyl, lower alkoxy, lower alkoxycarbonyl, lower halogenalkyl, lower halogenalkoxy, lower hydroxyalkyl, lower alkylsulfonyl and lower alkylsulfonylamino, and
   (7) pyridyl unsubstituted or substituted with one or two substituents independently selected from the group consisting of lower alkyl, lower alkoxy, cyano, morpholinyl and halogen.

10. A compound of claim 1, wherein $R^2$ is hydrogen.

11. A compound of claim 1, wherein $R^2$ is lower alkyl.

12. A compound of claim 1, wherein $R^2$ is phenyl unsubstituted or substituted with one to three substituents independently selected from the group consisting of lower alkyl, halogen and lower halogenalkyl.

13. A compound of claim 1, wherein $R^2$ is pyridyl which is unsubstituted or substituted with one or two substituents independently selected from the group consisting of lower alkyl and halogen.

14. A compound of claim 1, wherein $R^3$ is hydrogen.

15. A compound of claim 1, wherein G is

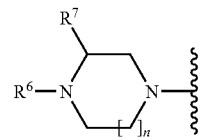

G1 wherein $R^6$ is lower alkyl, cycloalkyl, lower cycloalkylalkyl or a heterocyclic ring containing oxygen, $R^7$ is hydrogen, and n is 1 or 2.

16. A compound of claim 1, wherein $R^6$ is lower alkyl, cycloalkyl or tetrahydropyranyl.

17. A compound of claim 1, wherein $R^6$ is isopropyl.

18. A compound of claim 1, wherein n is 1.

19. A compound of claim 1, wherein n is 2.

20. A compound of claim 1, wherein G is

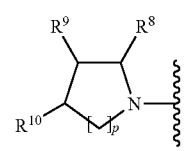

G2 wherein:
   p is 1 or 2;
   $R^8$ is hydrogen;
   $R^9$ and $R^{10}$ independently from each other are hydrogen or $-NR^{11}R^{12}$; and
   $R^{11}$ and $R^{12}$ independently from each other are lower alkyl or together with the nitrogen atom to which they are attached form a 5- or 6-membered saturated heterocyclic ring optionally containing a further heteroatom of nitrogen, oxygen or sulfur.

21. A compound of claim 1 selected from the group consisting of:
   [1-(2-chloro-pyridin-4-yl)-5-(4-isopropyl-piperazine-1-carbonyl)-1H-indol-2-yl]-(4-methanesulfonyl-piperazin-1-yl)-methanone,
   [1-(3-chloro-phenyl)-5-(4-isopropyl-piperazine-1-carbonyl)-1H-indol-2-yl]-[4-(piperidine-1-sulfonyl)-piperazin-1-yl]-methanone,
   (4-benzenesulfonyl-piperazin-1-yl)-[1-(3-chloro-phenyl)-5-(4-isopropyl-piperazine-1-carbonyl)-1H-indol-2-yl]-methanone,
   [1-(2-chloro-pyridin-4-yl)-5-(4-isopropyl-piperazine-1-carbonyl)-1H-indol-2-yl]-[4-(piperidine-1-carbonyl)-piperazin-1-yl]-methanone,
   4-[1-isopropyl-5-(4-isopropyl-[1,4]diazepane-1-carbonyl)-1H-indole-2-carbonyl]-piperazine-1-carboxylic acid ethyl ester,
   [1-isopropyl-5-(4-isopropyl-[1,4]diazepane-1-carbonyl)-1H-indol-2-yl]-(4-methanesulfonyl-piperazin-1-yl)-methanone,
   and any pharmaceutically acceptable salt thereof.

22. A pharmaceutical composition comprising a therapeutically effective amount of a compound of claim 1 and a pharmaceutically acceptable carrier.

* * * * *